US012712060B2

(12) United States Patent
Emaminejad et al.

(10) Patent No.: US 12,712,060 B2
(45) Date of Patent: Aug. 18, 2026

(54) MULTI-MODAL CRYPTO/BIO-HUMAN-MACHINE INTERFACE

(71) Applicant: The Regents of the University of California, Oakland, CA (US)

(72) Inventors: Sam Emaminejad, Los Angeles, CA (US); Shuyu Lin, Los Angeles, CA (US); Jialun Zhu, Los Angeles, CA (US); Wenzhuo Yu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/843,201

(22) PCT Filed: Mar. 2, 2023

(86) PCT No.: PCT/US2023/014397
§ 371 (c)(1),
(2) Date: Aug. 30, 2024

(87) PCT Pub. No.: WO2023/168011
PCT Pub. Date: Sep. 7, 2023

(65) Prior Publication Data

US 2025/0191718 A1 Jun. 12, 2025

Related U.S. Application Data

(60) Provisional application No. 63/399,615, filed on Aug. 19, 2022, provisional application No. 63/316,334, filed on Mar. 3, 2022.

(51) Int. Cl.
*G16H 20/13* (2018.01)
*G06F 3/01* (2006.01)
(Continued)

(52) U.S. Cl.
CPC ............ *G16H 20/13* (2018.01); *G06F 3/011* (2013.01); *G06F 21/32* (2013.01); *G16H 50/30* (2018.01)

(58) Field of Classification Search
CPC ........ G16H 20/13; G16H 50/30; G16H 20/10; G16H 20/70; G06F 3/011; G06F 21/32;
(Continued)

(56) References Cited

U.S. PATENT DOCUMENTS 11,442,071 B2 * 9/2022 Halpern ............ G01N 27/3275
2010/0237992 A1 * 9/2010 Liautaud ........... G06V 40/1306 340/5.83

(Continued)

FOREIGN PATENT DOCUMENTS

WO WO-2021081118 A1 * 4/2021 .......... H04L 9/0866

OTHER PUBLICATIONS

W. Yang et al., "Securing Mobile Healthcare Data: A Smart Card Based Cancelable Finger-Vein Bio-Cryptosystem," in IEEE Access, vol. 6, pp. 36939-36947, 2018, doi: 10.1109/ACCESS.2018. 2844182 (Year: 2018).*

(Continued)

*Primary Examiner* — Sun M Li
(74) *Attorney, Agent, or Firm* — Foley & Lardner LLP

(57) ABSTRACT

The present embodiments relate to a multimodal cryptographic bio-human machine interface ("CB-HMI"), which seamlessly translates the user's touch-based entries into encrypted biochemical, biophysical, and biometric indices. The CB-HMI features thin hydrogel-coated chemical sensors and inference algorithms to non-invasively and inconspicuously acquire biochemical indices such as circulating molecules that partition onto the skin (here, ethanol and acetaminophen). Additionally, the CB-HMI hosts physical sensors and associated algorithms to simultaneously acquire (Continued)

the user's heart rate, blood oxygen level, and fingerprint minutiae pattern. Additional or alternative embodiments include a touch-based non-invasive monitoring solution for lithium pharmacotherapy management. The system is constructed based on a thin organohydrogel-coated lithium ion-selective electrode (TOH-ISE), where the TOH coating was engineered to render stabilized conditions for sensing. In particular, by adopting a water glycerol bi-solvent matrix, the gel features antidehydration property, rendering a controlled micro-environment for the ISE to condition and minimized the signal drift.

19 Claims, 27 Drawing Sheets

(51) Int. Cl.
*G06F 21/32* (2013.01)
*G16H 50/30* (2018.01)

(58) Field of Classification Search
CPC ............ A61B 5/14517; A61B 5/02416; A61B 5/14546; A61B 5/4833; A61B 2503/22; A61B 5/1172; A61B 5/1486; A61B 5/4845; H04L 9/0866; H04L 9/3231
See application file for complete search history.

(56) References Cited

U.S. PATENT DOCUMENTS

2014/0204444 A1* 7/2014 Choi ..................... G02F 1/1524 359/275
2017/0245759 A1* 8/2017 Jain ...................... A61B 5/0077
2017/0325724 A1* 11/2017 Wang ................... A61B 5/6833
2018/0136247 A1* 5/2018 Boutelle .......... G01N 35/00693
2019/0117132 A1* 4/2019 Beech .................. A61B 5/1477
2021/0118579 A1* 4/2021 Morris ................ H04L 63/0838
2021/0186417 A1* 6/2021 Braig ................... A61B 5/7475

OTHER PUBLICATIONS

Darwish A, Hassanien AE. Wearable and implantable wireless sensor network solutions for healthcare monitoring. Sensors (Basel). 2011;11(6):5561-95. doi: 10.3390/s110605561. Epub May 26, 2011. Erratum in: Sensors (Basel). 2012;12(9):12375-6. PMID: 22163914; PMCID: PMC3231450. (Year: 2021).*
Gorey, Colm, New Sensor could massively changes lives of those with bipolar disorder, Machine, Aug. 29, 2018. (Year: 2018).*
W. Yang et al., "Securing Mobile Healthcare Data: A Smart Card Based Cancelable Finger-Vein Bio-Cryptosystem," in IEEE Access, vol. 6, pp. 36939-36947, 2018, doi: 10.1109/ACCESS.2018.2844182 (Year: 2018) (Year: 2018).*
Darwish A, Hassanien AE. Wearable and implantable wireless sensor network solutions for healthcare monitoring. Sensors (Basel). 2011;11(6):5561-95. doi: 10.3390/s110605561. Epub May 26, 2011. Erratum in: Sensors (Basel). 2012;12(9):12375-6. PMID: 22163914; PMCID: PMC3231450. (Year: 2021) (Year: 2021).*
Gorey, Colm, New Sensor could massively changes lives of those with bipolar disorder, Machine, Aug. 29, 2018. (Year: 2018) (Year: 2018).*
Foreign Action other than Search Report on PCT dtd Aug. 17, 2023.
Gorey, "New Sensor Could Massively Change Lives of Those with Bipolar Disorder," 2018, <URL: https://www.siliconrepublic.com/machines/bipolar-disorder-lithium-sensor> 2 pages.
International Search Report and Written Opinion on International Application No. PCT/US2023/014397 dated Nov. 2, 2023.

* cited by examiner

| Analyte | Concentration |
|---|---|
| Glucose | 50 μM |
| Lactate | 5 mM |
| NaCl | 10 mM |
| KCl | 2.4 mM |
| AA | 10 μM |
| UA | 25 μM |
| Ethanol | 0.5 mM |

| Analyte | Concentration |
|---|---|
| APAP | 5 μM |
| AA | 10 μM |
| UA | 25 μM |
| Tyr | 20 μM |
| Trp | 10 μM |
| EtOH | 1 mM |

| Fingerprint | Minutiae | Biometric key | Input |
|---|---|---|---|
| | | [105, 292, 304, 351, 397, 468, 479, 538, 549, 854] | 61234567890 |

| Fingerprint | Minutiae | Biometric key | Output |
|---|---|---|---|
| | | [81, 304, 351, 374, 409, 456, 468, 514, 549, 702] | 1234567890 |
| | | [93, 292, 304, 351, 397, 456, 468, 503, 526, 666] | 1234567890 |
| | | [0, 117, 175, 187, 234, 304, 421, 561, 585, 760] | Fail |
| | | [257, 362, 374, 549, 573, 596, 608, 690, 702, 1017] | Fail |

FIG. 16

MULTI-MODAL CRYPTO/BIO-HUMAN-MACHINE INTERFACE

CROSS-REFERENCE TO RELATED APPLICATIONS

The present application is a United States National Stage Patent Application under 35 U.S.C. § 371 of PCT/US2023/014397, filed Mar. 2, 2023, which claims priority to U.S. Provisional Application Nos. 63/316,334 filed Mar. 3, 2022, and 63/399,615 filed Aug. 19, 2022, the contents of which are incorporated herein by reference in their entirety.

STATEMENT OF FEDERALLY SPONSORED RESEARCH

This invention was made with government support under Grant Number 1722972, awarded by National Science Foundation. The government has certain rights in the invention.

TECHNICAL FIELD

The present embodiments relate generally to monitoring biological status and more particularly to methods and apparatuses for translating a user's touch-based entries into encrypted biochemical, biophysical, and biometric indices, optionally including an organohydrogel-based one-touch sensing interface for lithium therapy monitoring.

BACKGROUND

The awareness of the individuals' biological status is beneficial for creating interactive and adaptive environments that can actively assist the users to achieve optimal outcomes. Accordingly, specialized human machine interfaces—equipped with bio-perception and interpretation capabilities—are desired.

It is against this technological backdrop that the present Applicant sought a technological solution to these and other problems rooted in this technology.

SUMMARY

The present embodiments provide a multimodal cryptographic bio-human machine interface ("CB-HMI"), which seamlessly translates the user's touch-based entries into encrypted biochemical, biophysical, and biometric indices. The CB-HMI according to embodiments features thin hydrogel-coated chemical sensors and inference algorithms to non-invasively and inconspicuously acquire biochemical indices such as circulating molecules that partition onto the skin such as ethanol and acetaminophen. Additionally, the CB-HMI hosts physical sensors and associated algorithms to simultaneously acquire the user's heart rate, blood oxygen level, and fingerprint minutiae pattern. Methods according to embodiments include acquiring physiologically-relevant readouts of target bio-indices, as well as user-identifying and biometrically-encrypting/decrypting these indices in-situ (leveraging the fingerprint feature). The CB-HMI of embodiments provides new interactive solutions, which can be applied in the context of driving safety and medication use. For example, a vehicle activation system and a medication dispensing system including an integrated CB-HMI enables user bio-authentication (on the basis of the user's biological state and identity) prior to rendering the intended services.

Additional or alternative embodiments relate to decentralized lithium therapy management, including a touch-based non-invasive lithium monitoring solution, which centers on a gel-coated lithium sensing interface to collect and analyze the partitioned lithium ions on fingertips in-situ. This interface can be constructed using a thin organohydrogel-coated lithium ion-selective electrode (TOH-ISE), which features a uniquely developed TOH that simultaneously addresses stability challenges associated with the sensor and the sensing modality.

BRIEF DESCRIPTION OF THE DRAWINGS

These and other aspects and features of the present embodiments will become apparent to those ordinarily skilled in the art upon review of the following description of specific embodiments in conjunction with the accompanying figures, wherein:

FIG. 16 illustrates example aspects of biometric-encryption/decryption of a hypothetical input according to embodiments.

DETAILED DESCRIPTION

Figure 1:
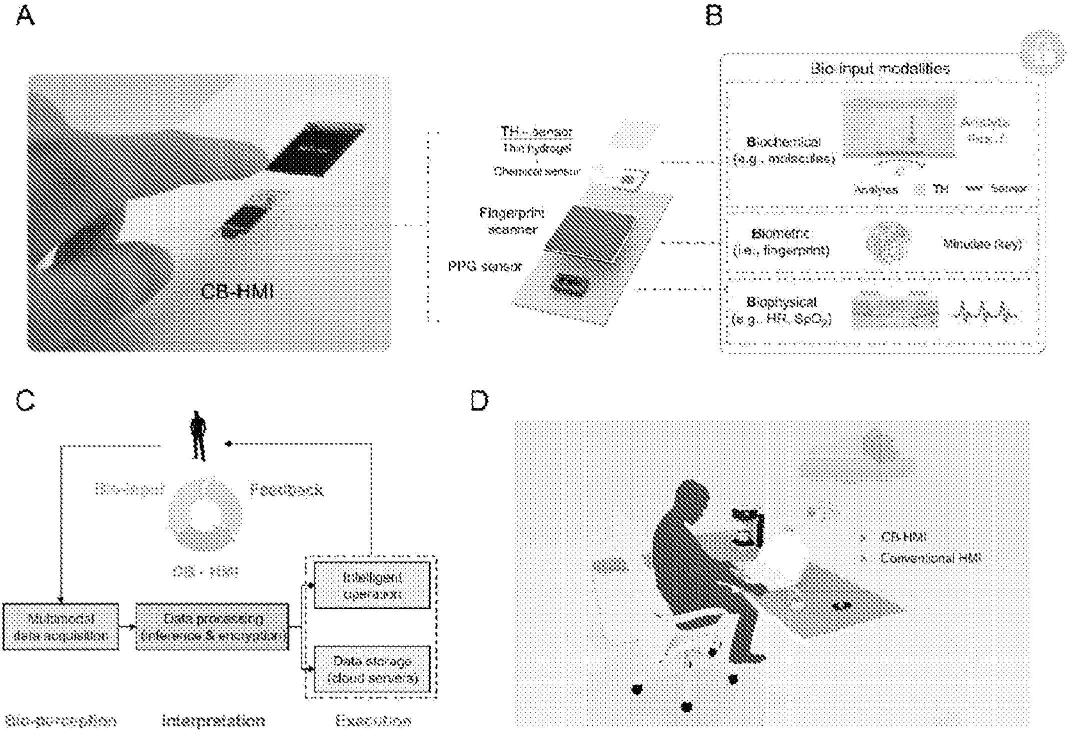
FIGS. 1A to 1D illustrate example aspects of enabling bio-perception and interpretation via CB-HMI according to embodiments.

The present embodiments will now be described in detail with reference to the drawings, which are provided as illustrative examples of the embodiments so as to enable those skilled in the art to practice the embodiments and alternatives apparent to those skilled in the art. Notably, the figures and examples below are not meant to limit the scope of the present embodiments to a single embodiment, but other embodiments are possible by way of interchange of some or all of the described or illustrated elements. Moreover, where certain elements of the present embodiments can be partially or fully implemented using known components, only those portions of such known components that are necessary for an understanding of the present embodiments will be described, and detailed descriptions of other portions of such known components will be omitted so as not to obscure the present embodiments. Embodiments described as being implemented in software should not be limited thereto, but can include embodiments implemented in hardware, or combinations of software and hardware, and vice-versa, as will be apparent to those skilled in the art, unless otherwise specified herein. In the present specification, an embodiment showing a singular component should not be considered limiting; rather, the present disclosure is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present embodiments encompass present and future known equivalents to the known components referred to herein by way of illustration.

Introduction

Human machine interfaces (HMIs)—with built-in data acquisition, processing capabilities and data security measures—are necessary for acquiring awareness of the individuals' status and assisting them with achieving optimal outcomes. Accordingly, various classes of HMIs have been developed and integrated within the ubiquitous electronics ecosystem to capture user-specific inputs through various channels, including touch (P. Bach-y-Rita, S. W. Kercel, Sensory substitution and the human-machine interface. Trends Cogn. Sci. 7, 541-546 (2003)), voice (CC. Philip R., S. L. Oviatt, The role of voice input for human-machine communication. Proc. Natl. Acad. Sci. U.S.A. 92, 9921-9927 (1995)), and gesture (Heikenfeld S. S. Rautaray, A. Agrawal, Vision based hand gesture recognition for human computer interaction: a survey. Artif. Intell. Rev. 43, 1-54 (2015); and Z. Zhou, K. Chen, X. Li, S. Zhang, Y. Wu, Y. Zhou, K. Meng, C. Sun, Q. He, W. Fan, E. Fan, Z. Lin, X. Tan, W. Deng, J. Yang, J. Chen, Sign-to-speech translation using machine-learning-assisted stretchable sensor arrays. Nat. Electron. 3, 571-578 (2020)). Such HMI modalities have laid the foundation for emerging technologies such as robotics (S. DiMaio, M. Hanuschik, U. Kreaden, "The Da Vinci Surgical System" in Surgical robotics: Systems applications and visions, J. Rosen, B. Hannaford, R. M. Satava, Eds. (Springer, Boston, MA, 2011), pp. 199-217), smart home (L. Jiang, D.-Y. Liu, B. Yang, "Smart home research" in Proceedings of 2004 International Conference on Machine Learning and Cybernetics (IEEE Cat. No. 04EX826) (2004), vol. 2, pp. 659-663 vol. 2), autonomous driving (K. Bengler, M. Rettenmaier, N. Fritz, A. Feierle, From HMI to HMIs: towards an HMI framework for automated driving. Information. 11, 61 (2020)), and augmented reality (X. Yu, Z. Xie, Y. Yu, J. Lee, A. Vazquez-Guardado, H. Luan, J. Ruban, X. Ning, A. Akhtar, D. Li, B. Ji, Y. Liu, R. Sun, J. Cao, Q. Huo, Y. Zhong, C. Lee, S. Kim, P. Gutruf, C. Zhang, Y. Xue, Q. Guo, A. Chempakasseril, P. Tian, W. Lu, J. Jeong, Y. Yu, J. Cornman, C. Tan, B. Kim, K. Lee, X. Feng, Y. Huang, J. A. Rogers, Skin-integrated wireless haptic interfaces for virtual and augmented reality. Nature. 575, 473-479 (2019)), which are already transforming our current ways of living.

However, these HMIs provide limited awareness of the individuals' biological status, which in turn prohibits their utility to unlock broader applications such as those in the healthcare domain (M. Mayer, A. J. Baeumner, A megatrend challenging analytical chemistry: biosensor and chemosensor concepts ready for the internet of things. Chem. Rev. 119, 7996-8027 (2019)). This limitation is because of their intrinsic shortcomings in collectively accessing informative biochemical and biophysical indices—in other words, they lack "biological perception". Toward devising a suitable HMI modality that bypasses such shortcomings, a key point of consideration is that biochemical indices (e.g., circulating biomarker molecules) are not trivially accessible due to the natural skin barrier function (J. Heikenfeld, A. Jajack, B. Feldman, S. W. Granger, S. Gaitonde, G. Begtrup, B. A. Katchman, Accessing analytes in biofluids for peripheral biochemical monitoring. Nat. Biotechnol. 37, 407-419 (2019))—in contrast to putative biophysical indices (e.g., heart rate), which can be accessed inconspicuously using existing HMI-compatible sensors (e.g., optical devices). Also relevant to the context at hand, given the personal and sensitive nature of the target indices, any devised bio-centered HMI modality should account for user identification and data protection (e.g., encryption) (A. D. Thierer, "The internet of things and wearable technology: addressing privacy and security concerns without derailing innovation" (SSRN Scholarly Paper ID 2494382, Social Science Research Network, Rochester, NY, 2015); and W. Wilkowska, M. Ziefle, Privacy and data security in E-health: requirements from the user's perspective).

To this end, fingertips could serve as ideal human body sites for engineering the envisioned HMI for numerous reasons. Firstly, many of the circulating biomarker molecules partition onto the skin surface of the fingertip (primarily via natural perspiration) with a relatively high flux (P. P. Samant, M. M. Niedzwiecki, N. Raviele, V. Tran, J. Mena-Lapaix, D. I. Walker, E. I. Felner, D. P. Jones, G. W. Miller, M. R. Prausnitz, Sampling interstitial fluid from human skin using a microneedle patch. Sci. Transl. Med. 12 (2020); H. Y. Y. Nyein, M. Bariya, B. Tran, C. H. Ahn, B. J. Brown, W. Ji, N. Davis, A. Javey, A wearable patch for continuous analysis of thermoregulatory sweat at rest. Nat. Commun. 12, 1823 (2021); K. C. O'Neill, P. Hinners, Y. Jin Lee, Potential of triacylglycerol profiles in latent fingerprints to reveal individual diet, exercise, or health information for forensic evidence. Anal. Methods. 12, 792-798 (2020); W. Tang, L. Yin, J. R. Sempionatto, J.-M. Moon, H. Teymourian, J. Wang, Touch-based stressless cortisol sensing. Adv. Mater. 33, 2008465 (2021); J. Brunmair, A. Bileck, T. Stimpfl, F. Raible, G. Del Favero, S. M. Meier-Menches, C. Gerner, Metabo-tip: a metabolomics platform for lifestyle monitoring supporting the development of novel strategies in predictive, preventive and personalised medicine. EPMA Journal. 12, 141-153 (2021)). Leveraging this phenomenon, we previously introduced a thin hydrogel-based sensing modality to noninvasively acquire such biochemical indices at the point of fingertip (S. Lin, B. Wang, Y. Zhao, R. Shih, X. Cheng, W. Yu, H. Hojaiji, H. Lin, C. Hoffman, D. Ly, J. Tan, Y. Chen, D. Di Carlo, C. Milla, S. Emaminejad, Natural perspiration sampling and in situ electrochemical analysis with hydrogel micropatches for user-identifiable and wireless chemo/biosensing. ACS Sens. 5, 265-273 (2020)). The inconspicuous nature of this sampling method allows for bypassing the challenges associated with conventional biomarker sampling modalities, which are invasive (e.g., fingerstick blood sampling), require external stimulation (e.g., iontophoretic sweat or interstitial fluid sampling (S. Emaminejad, W. Gao, E. Wu, Z. A. Davies, H. Yin Yin Nyein, S. Challa, S. P. Ryan, H. M. Fahad, K. Chen, Z. Shahpar, S. Talebi, C. Milla, A. Javey, R. W. Davis, Autonomous sweat extraction and analysis applied to cystic fibrosis and glucose monitoring using a fully integrated wearable platform. Proc. Natl. Acad. Sci. U.S.A. 114, 4625-4630 (2017); S. Mitragotri, M. Coleman, J. Kost, R. Langer, Analysis of ultrasonically extracted interstitial fluid as a predictor of blood glucose levels. J. Appl. Physiol. 89, 961-966 (2000); H. Lin, J. Tan, J. Zhu, S. Lin, Y. Zhao, W. Yu, H. Hojaiji, B. Wang, S. Yang, X. Cheng, Z. Wang, E. Tang, C. Yeung, S. Emaminejad, A programmable epidermal microfluidic valving system for wearable biofluid management and contextual biomarker analysis. Nat. Commun. 11, 4405 (2020)), and/or deviate from individuals' routine behavior (e.g., drooling for saliva collection). Secondly, clinically significant biophysical indices such as heart rate (HR) and oxygen saturation level ($SpO_2$) can be simultaneously acquired from fingertips using standard non-invasive methods (e.g., photoplethysmography). Thirdly, the fingertip's unique biometric feature (i.e., fingerprint) can be leveraged for user identification and as a personalized cryptographic key for in-situ data encryption (D. Maltoni, D. Maio, A. K. Jain, S. Prabhakar, Handbook of fingerprint recognition (Springer, 2009)). And fourthly, fingertip-based interactions are already the primary mode of communication in the readily proliferated HMIs (e.g., touch-sensitive screens, console controllers, trackpads, and keyboards).

Accordingly, the present embodiments relate to a touch-based cryptographic bio-HMI (namely, CB-HMI), which simultaneously acquires user's biochemical, biophysical, and biometric indices (e.g. as bio-inputs) using dedicated multi-modal data acquisition and processing modules. The data acquisition module consists of: 1) a thin hydrogel-coated electrochemical sensor (hereinafter, referred to as TH-sensor) to measure target biomarker molecule flux onto the skin (characterized and validated by a mass-transport simulation model and a microfluidic artificial fingertip); 2) a photoplethysmography (PPG) sensor to track HR and $SpO_2$ level; 3) a fingerprint scanner to obtain the minutiae pattern (as a biometric index); and 4) the associated front-end circuitry for signal conditioning. The data processing module features inference algorithms to contextualize the readouts for decision making and user identification, as well as a biometric encryption algorithm to create a personalized key based on the imaged minutiae pattern for data encryption. In this way, the devised CB-HMI can render bio-perception and interpretation functionalities. Harnessing these functionalities, the CB-HMI can be augmented with other entities to determine and deliver the appropriate course of action (e.g. feedback). Example entities include robotic systems to facilitate intelligent machine operations (via mechanical/visual stimuli) and cloud servers (for data storage).

For example, FIG. 1A is an illustration of the translation of the user's touch-based entry into bio-inputs. Right: exploded view of the CB-HMI. FIG. 1B illustrates example Multimodal acquisition of bio-inputs at the fingertip: biochemical indices (e.g., molecules) via a TH-sensor, biophysical indices (e.g., HR, SpO2) via a PPG sensor, and biometric indices (i.e., fingerprint) via a fingerprint scanner. All the acquired bio-inputs are biometrically-encrypted in-situ. FIG. 1C illustrates an example CB-HMI operational workflow, including its augmentation with feedback mechanisms. FIG. 1D is an example conceptual illustration of an ecosystem of objects, equipped with CB-HMI and conventional HMIs (e.g., touchpad and camera), forming a smart surrounding.

To illustrate the utility of the devised CB-HMI, demonstrated was its application within two representative scenarios toward improving the individuals' quality of life: driving safety and medication use. To acquire the biochemical index relevant to each of the scenarios, developed and employed were specialized TH-sensors. Specifically, devised was an enzymatic TH-sensor to target ethanol for the determination of alcohol intake and a voltammetric TH-sensor to target acetaminophen (APAP) as a model medication (a widely used analgesic and antipyretic). By incorporating such TH-sensors in human subject validation studies, demonstrated was the physiological significance of the acquired biochemical indices (on fingertip)—specifically, the correlation of the readings to the target molecules' circulating levels.

For the driving safety scenario, embodiments integrate the CB-HMI within an in-vehicle interactive system, which is capable of bio-authenticating the drivers (on the basis of the driver's biometric match and alcohol-free state) for vehicle activation, as well as alerting the driver to potential drowsiness. For the medication use scenario, embodiments integrate the CB-HMI within a custom-developed pill case to realize an unprecedented crypto-smart medication dispensing robotic system. This system uniquely bio-authenticates the user prior to supplying the medication, verifies the medication intake (both based on the biometric match and the detected drug-level), and logs the biometrically-encrypted record of the events and bio-inputs on a cloud-connected server.

These demonstrated applications illustrate the CB-HMI's capability in upgrading the surrounding objects to attain biological perception. The ubiquitous proliferation of the CB-HMI, together with other classes of intelligent HMIs, can ultimately create smart surroundings equipped with comprehensive and deep awareness of the individuals' psychophysiological state and needs (FIG. 1D).

In accordance with additional or alternative aspects, the present Applicant further recognizes that lithium salt is one of the most widely-used psychiatric medications for individuals with bipolar disorder (Shorter, E. The History of Lithium Therapy. Bipolar Disorders 2009, 11 (s2), 4-9. https://doi.org/10.1111/j.1399-5618.2009.00706.x). Despite its demonstrated efficacy for mood stabilization, translating its effectiveness into improved patient outcomes in clinical practice remains nontrivial due to multiple challenges. Firstly, lithium has a narrow therapeutic window (~0.6-1.2 mM) with severe adverse effects if overdosed (Mitchell, P. B. Therapeutic Drug Monitoring of Psychotropic Medications. British Journal of Clinical Pharmacology 2001, 52 (S1), 45-54. https://doi.org/10.1111/j.1365-2125.2001.00174.x.). Secondly, due to the specific condition of the patient group and the medication itself (e.g., bipolar illness symptoms, drug's side effects), the adherence rate of lithium pharmacotherapy is low (~60%) (Lingam, R.; Scott, J. Treatment Non-Adherence in Affective Disorders. Acta Psychiatrica Scandinavica 2002, 105 (3), 164-172. https://doi.org/10.1034/j.1600-0447.2002. 1r084.x; Sajatovic, M.; Valenstein, M.; Blow, F.; Ganoczy, D.; Ignacio, R. Treatment Adherence With Lithium and Anticonvulsant Medications Among Patients With Bipolar Disorder. PS 2007, 58 (6), 855-863. https://doi.org/10.1176/ps.2007.58.6.855.). Poor adherence can lead to poor treatment outcomes associated with an increased risk of relapse, re-hospitalization, and suicide (Chakrabarti, S. Treatment-Adherence in Bipolar Disorder: A Patient-Centred Approach. World J Psychiatry 2016, 6 (4), 399-409. https://doi.org/10.5498/wjp.v6.i4.399). Standard practices of lithium monitoring for precise dosing are confined to centralized hospitals and involve invasive blood draw and high-cost lab-based analysis with a long turnaround time. Moreover, currently, there is no direct lithium adherence monitoring available, and the indirect monitoring solutions (e.g., pill counters) are incapable of verifying the actual intake event (inherently non-specific).

Wearable and mobile biochemical sensing technologies are suitable to overcome these limitations, because they can potentially be deployed at a large scale to monitor molecular-level information in a non-/minimally-invasive and real-time manner (Gao, W.; Emaminejad, S.; Nyein, H. Y. Y.; Challa, S.; Chen, K.; Peck, A.; Fahad, H. M.; Ota, H.; Shiraki, H.; Kiriya, D.; Lien, D.-H.; Brooks, G. A.; Davis, R. W.; Javey, A. Fully Integrated Wearable Sensor Arrays for Multiplexed in Situ Perspiration Analysis. Nature 2016, 529 (7587), 509-514. https://doi.org/10.1038/nature 16521; Bariya, M.; Nyein, H. Y. Y.; Javey, A. Wearable Sweat Sensors. Nat Electron 2018, 1 (3), 160-171. https://doi.org/10.1038/s41928-018-0043-v; Kim, J.; Campbell, A. S.; de Avila, B. E.-F.; Wang, J. Wearable Biosensors for Healthcare Monitoring. Nat Biotechnol 2019, 37 (4), 389-406. https://doi.org/10.1038/s41587-019-0045-y). Particularly, recent studies have shown that many circulating biomarker molecules partition onto the fingertip surface (primarily via natural perspiration) with a relatively high flux, which can be leveraged for inconspicuous biomonitoring (Moon, J.-M.; Teymourian, H.; De la Paz, E.; Sempionatto, J. R.; Mahato, K.; Sonsa-ard, T.; Huang, N.; Longardner, K.; Litvan, I.; Wang, J. Non-Invasive Sweat-Based Tracking of L-Dopa Pharmacokinetic Profiles Following an Oral Tablet Administration. Angewandte Chemie 2021, 133 (35), 19222-19226. https://doi.org/10.1002/ange.202106674; Nyein, H. Y. Y.; Bariya, M.; Tran, B.; Ahn, C. H.; Brown, B. J.; Ji, W.; Davis, N.; Javey, A. A Wearable Patch for Continuous Analysis of Thermoregulatory Sweat at Rest. Nat. Commun. 2021, 12 (1), 1823. https://doi.org/10.1038/s41467-021-22109-z; Ichimura, Y.; Kuritsubo, T.; Nagamine, K.; Nomura, A.; Shitanda, I.; Tokito, S. A Fully Screen-Printed Potentiometric Chloride Ion Sensor Employing a Hydrogel-Based Touchpad for Simple and Non-Invasive Daily Electrolyte Analysis. Anal Bioanal Chem 2021, 413 (7), 1883-1891. https://doi.org/10.1007/s00216-021-03156-3).

To adopt these opportunities for decentralized lithium therapy management, additional or alternative embodiments relate to a touch-based non-invasive lithium monitoring solution, which centers on a gel-coated lithium sensing interface to collect and analyze the partitioned lithium ions on fingertips in-situ. This interface can be constructed using a thin organohydrogel-coated lithium ion-selective electrode (TOH-ISE), which features a uniquely developed TOH that simultaneously addresses stability challenges associated with the sensor and the sensing modality.

Figure 20:
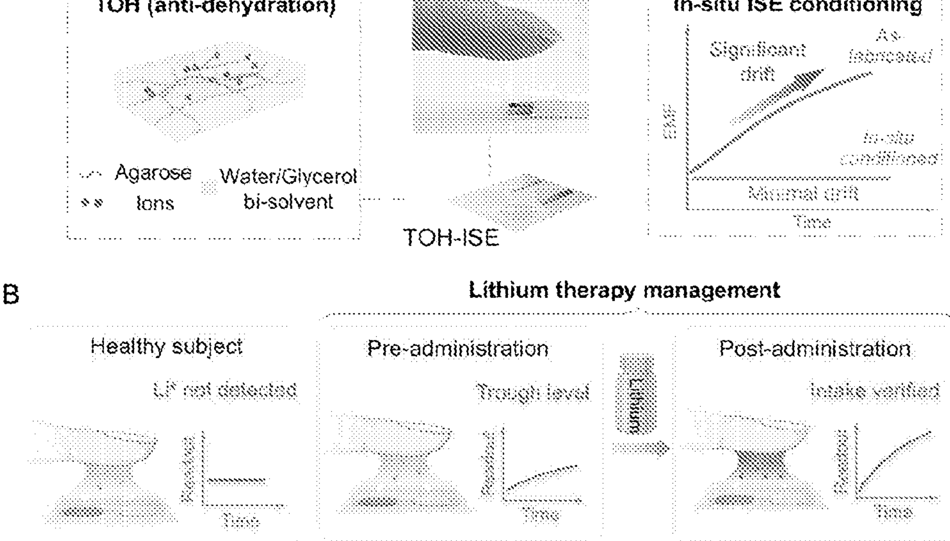
FIGS. 20A and 20B illustrate example aspects of touch-based lithium monitoring according to embodiments.

For example, in accordance with these aspects, FIG. 20A is an example schematic and optical image of a TOH-ISE interface (center). The left panel highlights the composition and the structure of a TOH with an anti-dehydration property. The right schematic shows minimal sensor drift with the aid of in-situ ISE conditioning. FIG. 20B illustrates an example application of the TOH-ISE interface for lithium therapy management.

To elaborate, from the sensing interface aspect, previously demonstrated touch-based sensors mainly use a hydrogel interface for analyte sampling from the fingertip. However, the rapid hydrogel dehydration complicates the device storage and usage (Lin, S.; Wang, B.; Zhao, Y.; Shih, R.; Cheng, X.; Yu, W.; Hojaiji, H.; Lin, H.; Hoffman, C.; Ly, D.; Tan, J.; Chen, Y.; Di Carlo, D.; Milla, C.; Emaminejad, S. Natural Perspiration Sampling and in Situ Electrochemical Analysis with Hydrogel Micropatches for User-Identifiable and Wireless Chemo/Biosensing. ACS Sens. 2019. https://doi.org/10.1021/acssensors.9b01727; Sempionatto, J. R.; Moon, J.-M.; Wang, J. Touch-Based Fingertip Blood-Free Reliable Glucose Monitoring: Personalized Data Processing for Predicting Blood Glucose Concentrations. ACS Sens. 2021, 6 (5), 1875-1883. https://doi.org/10.1021/acssensors.1c00139). From the ion-selective sensing aspect, prolonged ISE conditioning is usually required to render low-drift readouts (Shao, Y.; Ying, Y.; Ping, J. Recent Advances in Solid-Contact Ion-Selective Electrodes: Functional Materials, Transduction Mechanisms, and Development Trends. Chemical Society Reviews 2020, 49 (13), 4405-4465. https://doi.org/10.1039/C9CS00587K), which serves as a key challenge prohibiting their translation application. To overcome these challenges, by adopting a water-glycerol bi-solvent matrix, the devised TOH was endowed with an anti-dehydration property (Wu, Z.; Yang, X.; Wu, J. Conductive Hydrogel- and Organohydrogel-Based Stretchable Sensors. ACS Appl. Mater. Interfaces 2021, 13 (2), 2128-2144. https://doi.org/10.1021/acsami.0c21841; Wu, J.; Wu, Z.; Xu, H.; Wu, Q.; Liu, C.; Yang, B.-R.; Gui, X.; Xie, X.; Tao, K.; Shen, Y.; Miao, J.; K. Norford, L. An Intrinsically Stretchable Humidity Sensor Based on Anti-Drying, Self-Healing and Transparent Organohydrogels. Materials Horizons 2019, 6 (3), 595-603. https://doi.org/10.1039/C8MH01160E). When coupled with a lithium ISE, the TOH coating serves as a controlled micro-environment to condition the ISE in-situ. In this way, embodiments eliminate the need for extensive ISE conditioning and thus enable a "plug-and-sense" operation.

The developed TOH-ISE can be further augmented with a custom-developed ISE-specific signal interpretation framework—capable of extracting the lithium flux information from the touch-based readouts. The integrated lithium monitoring solution was then validated in both ex-situ and in-situ settings, by leveraging a custom-developed artificial fingertip setup and performing human subject studies, respectively. The demonstrated reliable lithium sensing capability illustrates the suitability of our touch-based solution for lithium adherence monitoring, and more broadly for managing the lithium-based pharmacotherapy (FIG. 20B).

Results

Development and Characterization of the Thin Hydrogel-Coated Electrochemical Sensors To access biochemical indices, which are central to the realization of bio-perception, engineered were specialized TH-sensors. TH-sensors present great potential for the sample-to-answer quantification of on-skin analyte flux—owing to their hydrogel coating, which serves both as a sampling and an electroanalysis medium. Embodiments adapt the TH-sensing capability to target ethanol and APAP. The choice of ethanol is motivated by the potential of its ubiquitous biomonitoring to enable timely intervention and prevention of harmful alcohol-related personal/societal outcomes such as driving under the influence (DUI) (World Health Organization, ProQuest (Firm), Global status report on road safety 2018 (World Health Organization, 2018)). Also, APAP serves as a model drug to illustrate the potential of TH-sensing for drug abuse/adherence monitoring. Given that APAP is a widely used analgesic and antipyretic, and its supratherapeutic administration is the leading cause of liver failure in the United States (A. M. Larson, J. Polson, R. J. Fontana, T. J. Davern, E. Lalani, L. S. Hynan, J. S. Reisch, F. V. Schiodt, G. Ostapowicz, A. O. Shakil, W. M. Lee, Acetaminophen-induced acute liver failure: results of a united states multicenter, prospective study. Hepatology. 42, 1364-1372 (2005)), APAP biomonitoring may be particularly beneficial to promote patient compliance and safety.

Figure 2:
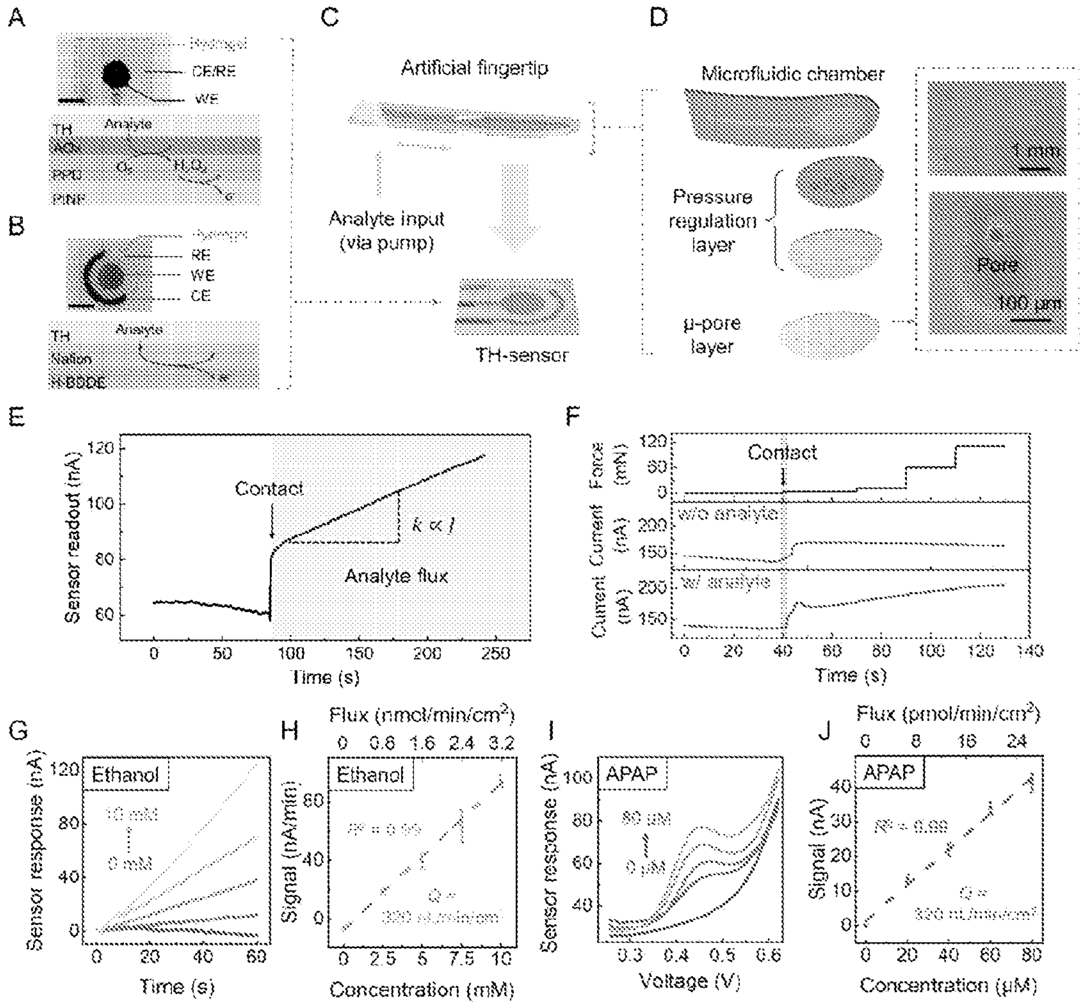
FIGS. 2A to 2J illustrate example aspects of development and ex-situ characterization of the TH-sensors according to embodiments.
Figure 21:
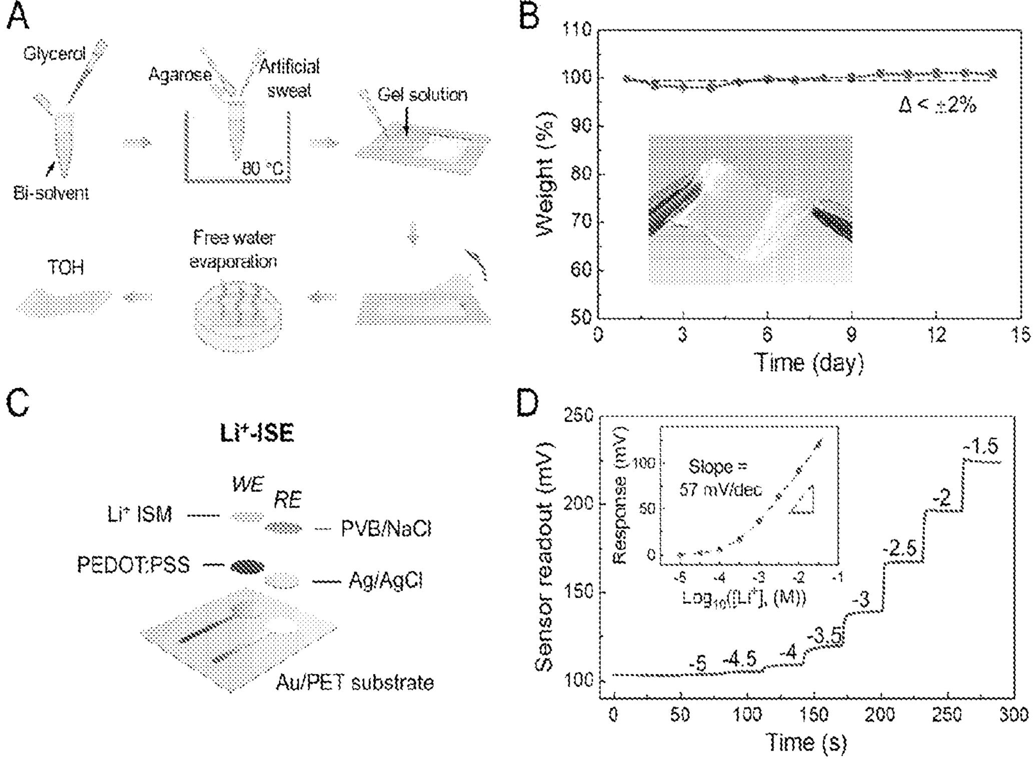
FIGS. 21A to 21D illustrate example aspects of characterization of individual components of the sensing interface according to embodiments.

FIGS. 2A to 2J illustrate example aspects of development and ex-situ characterization of the TH-sensors according to embodiments. FIGS. 2A and 2B provide Top-view photos and reaction schematics of the ethanol TH-sensor (A) and the APAP TH-sensor (B). WE, CE, and RE correspondingly denote working, counter, and reference electrodes. Scale bar: 2 mm. FIG. 2C illustrates Ex-situ characterization of the TH-sensor via a microfluidic artificial fingertip. FIG. 2D is an Exploded view of the artificial fingertip. Inset shows the optical images of the laser-patterned μ-pore layer (with two different zoom-in views). FIG. 2E provides an example Amperometric recording of an ethanol TH-sensor upon contact with an ethanol-contained artificial fingertip (concentration: 2 mM). FIG. 2F provides an example Amperometric recording of an ethanol TH-sensor in the presence of a varying pressing force profile. Top panel represents the exerted force profile. Middle and bottom panels correspondingly capture the measured TH-sensor's responses to the input fluid containing zero- and 2-mM ethanol. FIG. 2G provides an example Amperometric responses of an ethanol TH-sensor to input fluid with various ethanol concentrations (0, 2, 4, 6, 8, 10 mM, all post-contact with the artificial fingertip). FIG. 2H provides an example Ethanol TH-sensor calibration curve. Error bars indicate standard error (three trials). FIG. 21 provides example Differential pulse voltammograms of an APAP TH-sensor 3 min after the introduction of the input fluid with various APAP concentrations (0, 20, 40, 60, 80 μM). FIG. 2J provides an example APAP TH-sensor calibration curve. Error bars indicate standard error (three trials). For all the experiments the input fluid was based on a phosphate-buffered saline solution, injected at 320 nL/min/cm$^2$.

Figure 6:
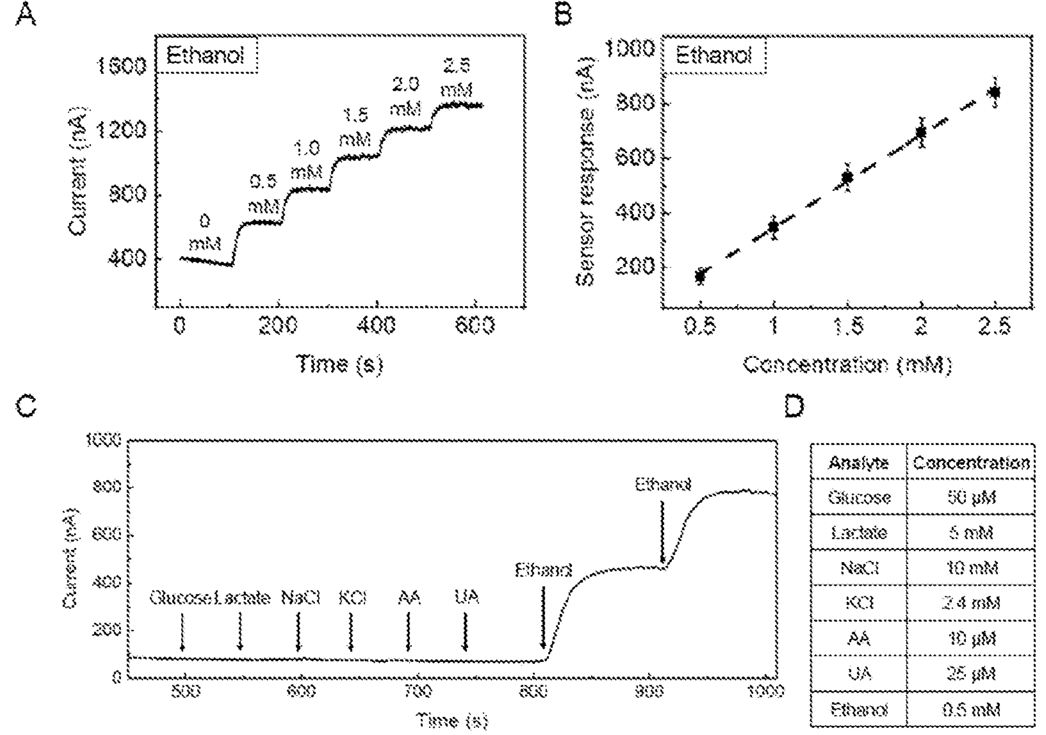
FIGS. 6A to 6D illustrate example aspects of characterization of the ethanol sensor according to embodiments.
Figure 7:
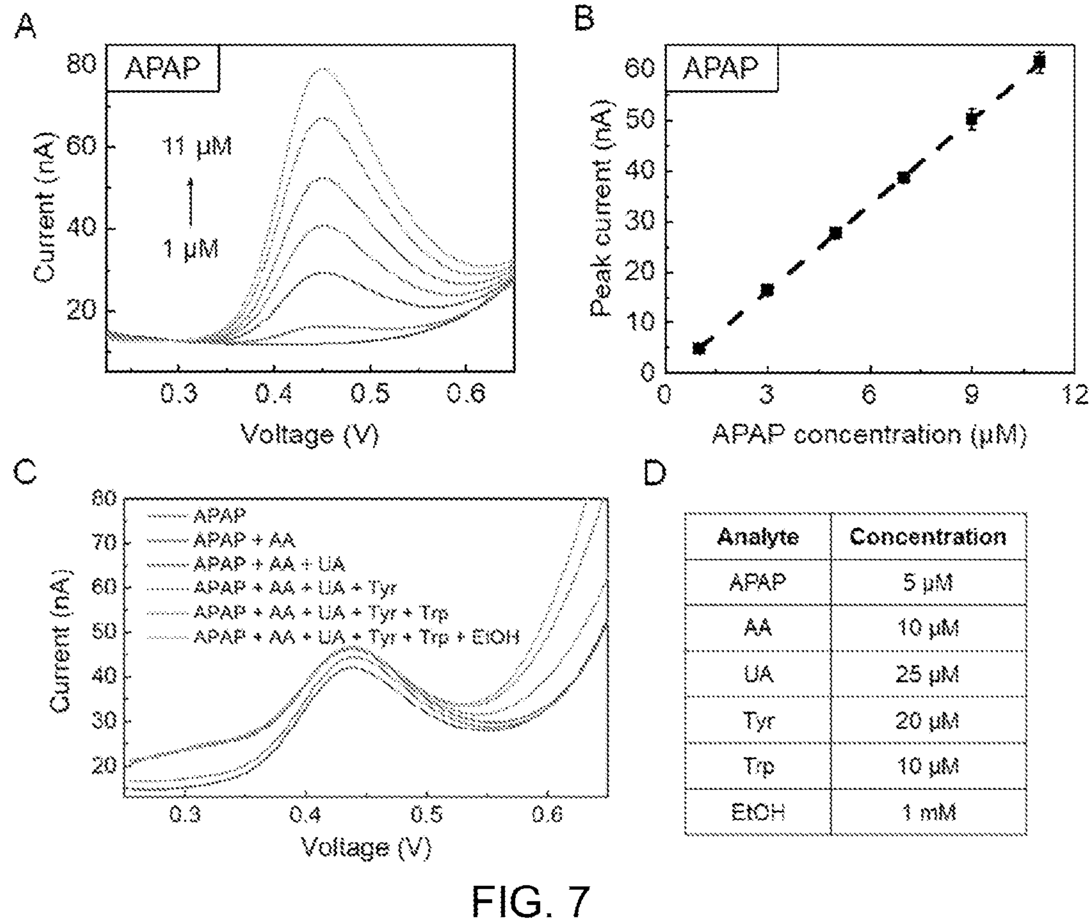
FIGS. 7A to 7D illustrate example aspects of characterization of the APAP sensor according to embodiments.

To construct the underlying sensing surfaces of the ethanol and APAP TH-sensors (FIGS. 2A, 2B), embodiments correspondingly utilized previously reported mediator-free electroenzymatic sensing and electroactive interference-free voltammetric methodologies (X. Cheng, B. Wang, Y. Zhao, H. Hojaiji, S. Lin, R. Shih, H. Lin, S. Tamayosa, B. Ham, P. Stout, K. Salahi, Z. Wang, C. Zhao, J. Tan, S. Emaminejad, A Mediator-Free Electroenzymatic Sensing Methodology to Mitigate Ionic and Electroactive Interferents' Effects for Reliable Wearable Metabolite and Nutrient Monitoring. Adv. Funct. Mater. 30, 1908507 (2020)). One example constructed ethanol sensor is comprised of: 1) an enzyme layer (alcohol oxidase, AOx) to catalyze the oxidation of ethanol and generate hydrogen peroxide ($H_2O_2$) as a detectable byproduct; 2) a permselective membrane (poly-m-phenylenediamine, PPD) to reject interfering electroactive species; and 3) an electroanalysis layer (platinum nanoparticle, PtNP) to detect the generated $H_2O_2$. The constructed APAP sensor is based on: 1) a polymeric coating (Nafion) to mitigate the interference of the electroactive species and enhance the biofouling resistance and 2) a voltammetric sensing electrode (hydrogen-terminated boron-doped diamond electrode, H-BDDE) to selectively detect the oxidation peak of APAP. FIGS. 6 and 7 show the linear response (limit of detection: 0.13 mM for ethanol, 0.12 M for APAP) and high selectivity of the developed sensing surfaces, demonstrating their suitability for the envisioned CB-HMI application.

More particularly, FIG. 6 illustrates example aspects of characterization of the ethanol sensor according to embodiments: (A) Real-time chronoamperometric current response of a representative ethanol sensor (performed in PBS). (B) Corresponding calibration plot. Error bars indicate standard error (n=3). (C) Comprehensive selectivity study: monitoring the sensor's chronoamperometric current response to the sequential introduction of the interfering and target analytes. (D) Table of analyte concentrations used in the selectivity study (within their concentration range in sweat). AA: ascorbic acid; UA: uric acid.

Moreover, FIG. 7 illustrates example aspects of characterization of the APAP sensor according to embodiments: (A) Differential pulse voltammograms of a representative APAP sensor (performed in PBS, containing 0, 1, 3, 5, 7, 9, 11 μM APAP). (B) Corresponding calibration plot. Error bars indicate standard error (n=3). (C) Comprehensive selectivity study: monitoring the sensor's DPV response to the sequential introduction of interfering (mainly electroactive) and target analytes. (D) Table of analyte concentrations used in the selectivity study (within their concentration range in sweat). AA: ascorbic acid; UA: uric acid; Tyr: Tyrosine; Trp: tryptophan; EtOH: ethanol.

Figure 8:
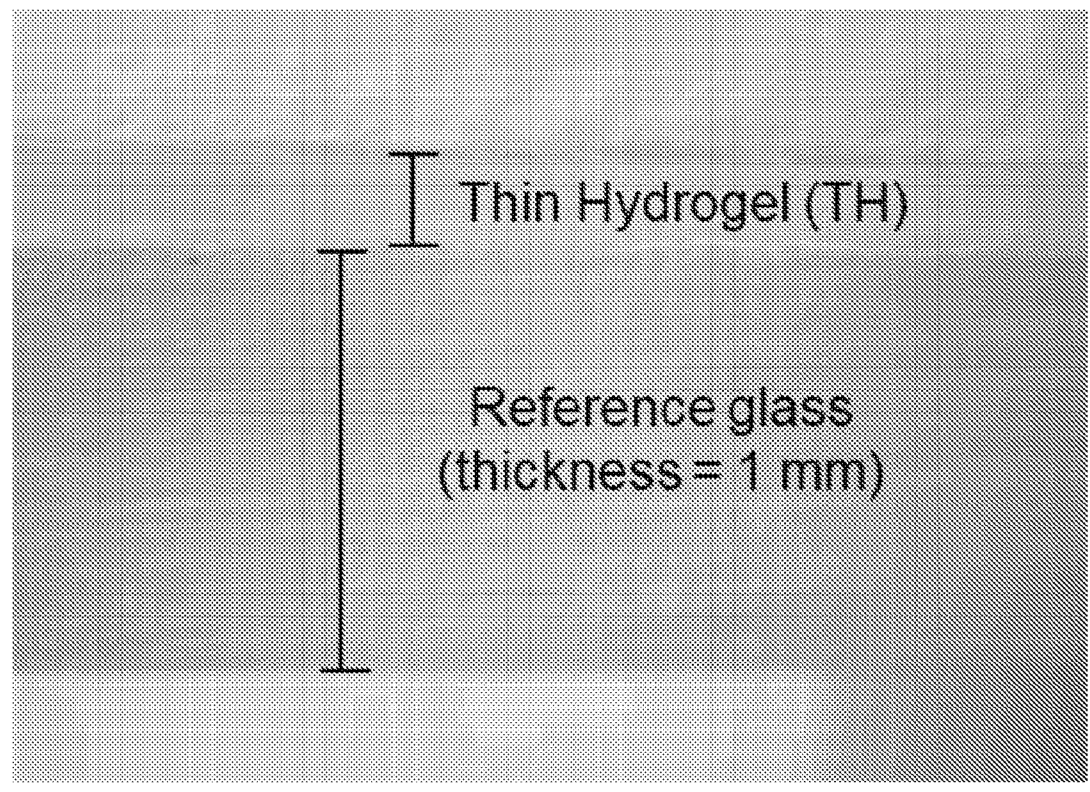
FIG. 8 is a photograph illustrating example aspects of thickness of the TH according to embodiments.

Once developed, the sensing surfaces were coupled with a thin hydrogel layer to form the envisioned TH-sensors. Here, the hydrogel layer was particularly thinned down (by introducing a rehydration step in the fabrication process, FIG. 8) to increase the accumulated analyte's end-concentration in the hydrogel medium and to shorten the response time. More particularly, FIG. 8 illustrates example aspects of thickness of the TH according to embodiments. It shows an Optical image of an example TH component on a glass slide. The measured TH thickness was 220±20 μm (n=10).

Figure 9:
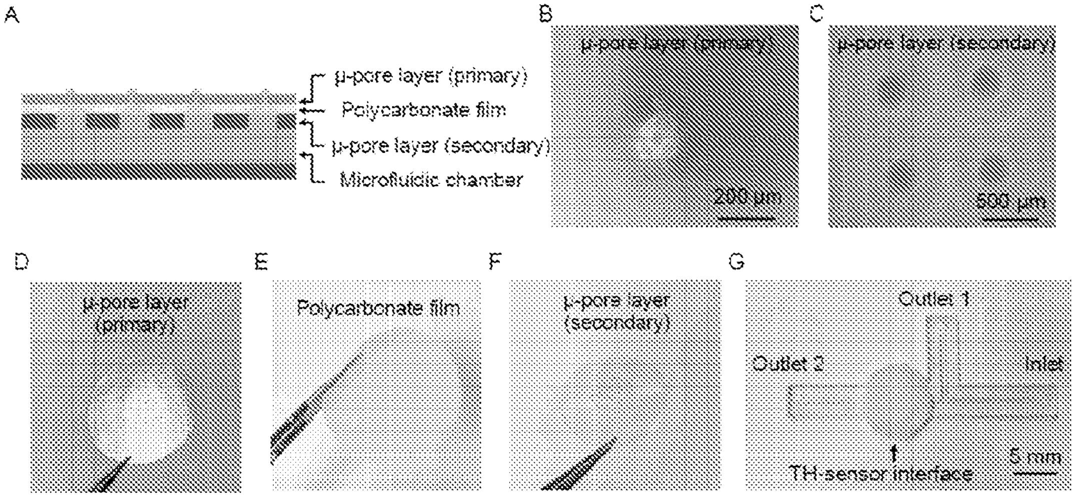
FIGS. 9A to 9G illustrate example aspects of structure of the microfluidic artificial fingertip according to embodiments.

To characterize the performance of the TH-sensors ex-situ, developed was a microfluidic artificial fingertip, emulating the analyte flux on a fingertip via natural perspiration (FIG. 2C, FIG. 9). More particularly, FIG. 9 illustrates example aspects of structure of the microfluidic artificial fingertip according to embodiments: (A) Side view schematic of the artificial fingertip. (B, C) Microscopic images of the primary (B) and secondary (C) μ-pore layers, showing the pore size and density of the laser-patterned pores. Primary: pore size: 48±5 m (n=10), density: 139 cm-2; secondary: pore size: 292±17 m (n=10), pore density: 139 cm-2. (D-F) Optical images of the primary t-pore layer (D, based on a scotch tape), the polycarbonate film (E), and the secondary μ-pore layer (F, based on a double-sided tape). (G) Optical image of an assembled microfluidic fingertip. The inlet is connected to a syringe pump. The two outlets are utilized for the microfluidic chamber flushing.

This setup is particularly useful for characterizing the TH-sensors' responses with respect to the analyte-related parameters (e.g., concentration, mass transport delivery rate) and CB-HMI-specific influential factors (e.g., fingertip mechanical contact force). The developed artificial fingertip in some embodiments comprises: 1) a microfluidic chamber to facilitate the delivery of the input fluids (with dynamically-varying composition and at adjustable flow rates) via a programmable pump (mimicking the thermoregulatory sweat secretion by the secretory coil); 2) a pressure regulation layer (L. Hou, J. Hagen, X. Wang, I. Papautsky, R. Naik, N. Kelley-Loughnane, J. Heikenfeld, Artificial microfluidic skin for in vitro perspiration simulation and testing. Lab Chip. 13, 1868-1875 (2013)), mimicking the highly fluidically-resistive sweat duct, to render a stable low flow rate (<1 μL/min/cm$^2$, corresponding to the natural perspiration rate (M. J. Patterson, S. D. R. Galloway, M. A. Nimmo, Variations in regional sweat composition in normal human males. Exp. Physiol. 85, 869-875 (2000)); and 3) a laser-patterned pore layer (with the pore size comparable with the sweat duct diameter, ~80 μm (S. R. Tripathi, E. Miyata, P. B. Ishai, K. Kawase, Morphology of human sweat ducts observed by optical coherence tomography and their frequency of resonance in the terahertz frequency region. Sci. Rep. 5, 9071 (2015)), mimicking the fingertip skin surface (to be interfaced with the TH-sensor).

Figure 10:
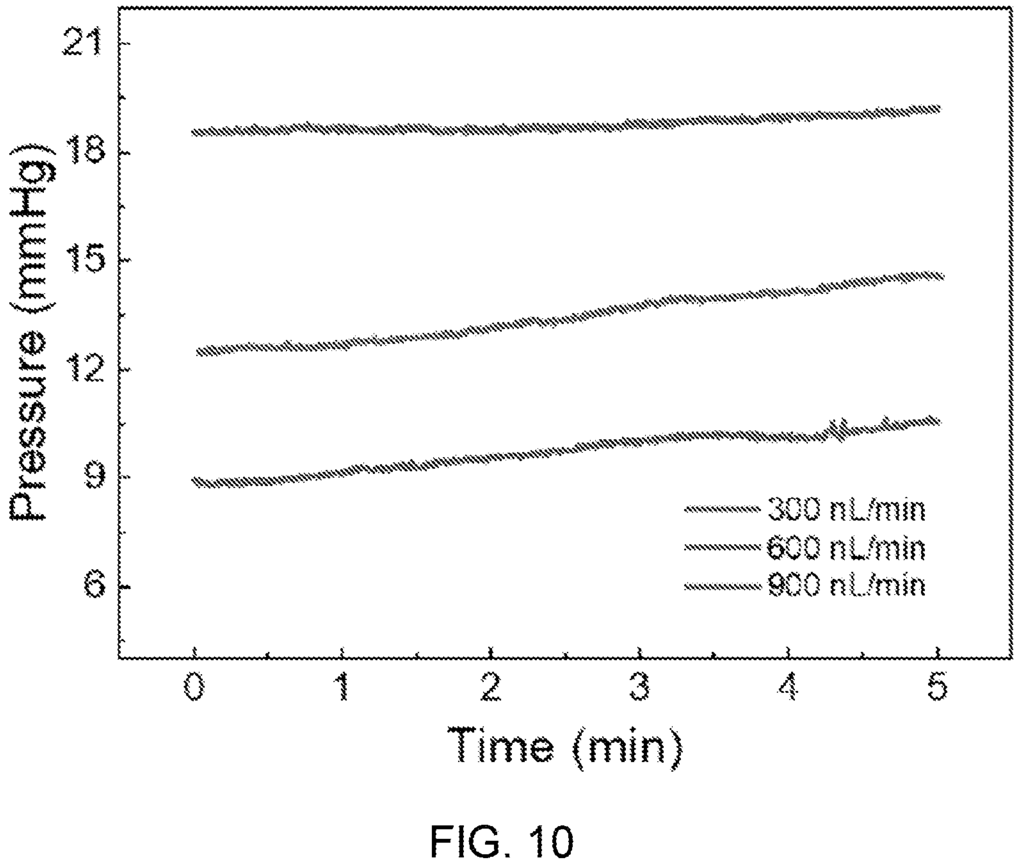
FIG. 10 is a graph illustrating example aspects of hydraulic pressure characterization of the microfluidic artificial fingertip according to embodiments.

To characterize the constructed artificial fingertip from the standpoint of fluid secretion, monitored was the hydraulic pressure across the microfluidic chamber, under various input flow rates. As can be seen in FIG. 10, for each of the flow rates, a relatively flat pressure profile was measured, indicating the artificial fingertip's microfluidic capability to reliably deliver the intended analyte flux within the expected range of secretion rate. More particularly, FIG. 10 illustrates example aspects of hydraulic pressure characterization of the microfluidic artificial fingertip according to embodiments. It shows Real-time recording of the steady state pressure across the artificial fingertip (with outlets 1 and 2 closed) at three input flow rates.

To characterize the TH-sensor's response in relation to the envisioned touch-introduced analyte flux, embodiments exploited the ethanol sensor, which allows for tracking its response in real-time via amperometry. Accordingly, embodiments interface the artificial fingertip with the ethanol TH-sensor and configure it to continuously deliver ethanol molecules at a set flux (here, 0.64 nmol/min/cm$^2$). Also utilized was a commercial benchtop potentiostat to record the generated sensor response. As illustrated in FIG. 2D, after an initial current jump (corresponding to the formation of the microfluidic fingertip/hydrogel contact), the sensor presented increasingly current response levels with a constant slope (denoted as k). The observed slope reflects the introduced analyte flux (J). That is because the sensor's response is directly related to the hydrogel-accumulated analyte concentration at the vicinity of the sensing surface, which increases with time in proportion to the net analyte flux. To verify this point, performed was a finite element analysis (FEA) by setting up a simulation model (using COMSOL software), mimicking the electrochemical sensing situation.

Figure 11:
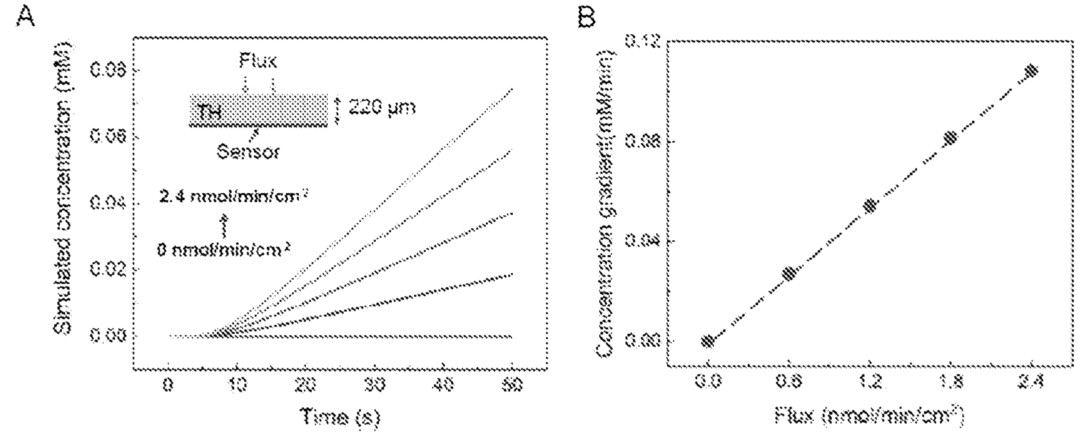
FIGS. 11A and 11B illustrate example aspects of FEA of the analyte concentration profile within the TH according to embodiments.

Specifically simulated was the analyte concentration profile (within a hydrogel layer) across time for different levels of analyte flux inputs. As shown in FIG. 11, for a given input flux, the analyte concentration level at the vicinity of the sensing surface increases linearly with time, where the observed slope for each case is proportional to the input flux. More particularly, FIG. 11 illustrates example aspects of FEA of the analyte concentration profile within the TH according to embodiments: (A) Simulated temporal profiles of analyte concentration at the vicinity of the sensor for various input flux levels. Inset shows the side view schematic of the FEA model. (B) Temporal concentration gradient (slope in FIG. 11A) versus input flux, illustrating a linear relationship.

Relevant to the envisioned touch-based sensing context, the same artificial fingertip characterization setup was utilized to investigate the potential confounding influence of variability in the strength of the pressing force. Accordingly, as the sensor response was being recorded continuously, different weights were mounted onto the artificial fingertip to mimic different strengths of pressing (corresponding to the normal pressure range exerted by finger pressing (M. Ayyildiz, M. Scaraggi, O. Sirin, C. Basdogan, B. N. J. Persson, Contact mechanics between the human finger and a touchscreen under electroadhesion. Proc. Natl. Acad. Sci. U.S.A. 115, 12668-12673 (2018))). As shown in FIG. 2F, while initially a current jump was observed when making a contact between the weight-mounted artificial fingertip and the TH-sensor, mounting additional weights did not significantly alter the sensor response. In particular, zero slope was consistently measured in the absence of analyte flux (i.e., using a blank buffer solution as fluid input) and a relatively unchanged finite slope was observed for the case of non-zero analyte flux. These results suggest that the measured analyte flux is practically unaffected by the fingertip pressing force variability.

Furthermore, the artificial fingertip was utilized to systematically validate the TH-sensor's ability to track the analyte flux for varying introduced analyte concentration and flow rate conditions (where the analyte flux is the product of the latter two parameters). In our context, given the exogenous nature of the target analytes, the relative variations in analyte concentration (during the course of analyte circulation) is more significant than the relative changes in the natural perspiration rate (which in stationary settings is relatively stable (U. Jacobi, J. Bartoll, W. Sterry, J. Lademann, Orally administered ethanol: transepidermal pathways and effects on the human skin barrier. Arch. Dermatol. Res. 296, 332-338 (2005)). Therefore, for this study, we primarily focused on modulating the analyte concentration, while fixing the input flow rate within the physiologically-relevant range.

FIG. 2G shows the real-time amperometric readouts of the ethanol TH-sensor, where the observed slopes linearly scale with the input concentrations (concentration range:

0-10 mM, flow rate: 320 nL/min/cm$^2$). FIG. 2H illustrates the corresponding calibration curve constructed based on the measured slopes (R2=0.99). To characterize the APAP TH-sensor, captured were the sensor's voltammograms (3 min after the sample introduction) for the APAP concentrations ranging from 0 to 80 μM (introduced at the same aforementioned flow rate, FIG. 2I). For each case, the voltammetric peak height (serving as the voltammetric signal) was extracted by applying our previously reported analytical framework and correcting for the effect of baseline variation. FIG. 2J shows the highly linear relationship between the input APAP concentration and the extracted signal (R2=0.99).

Figure 12:
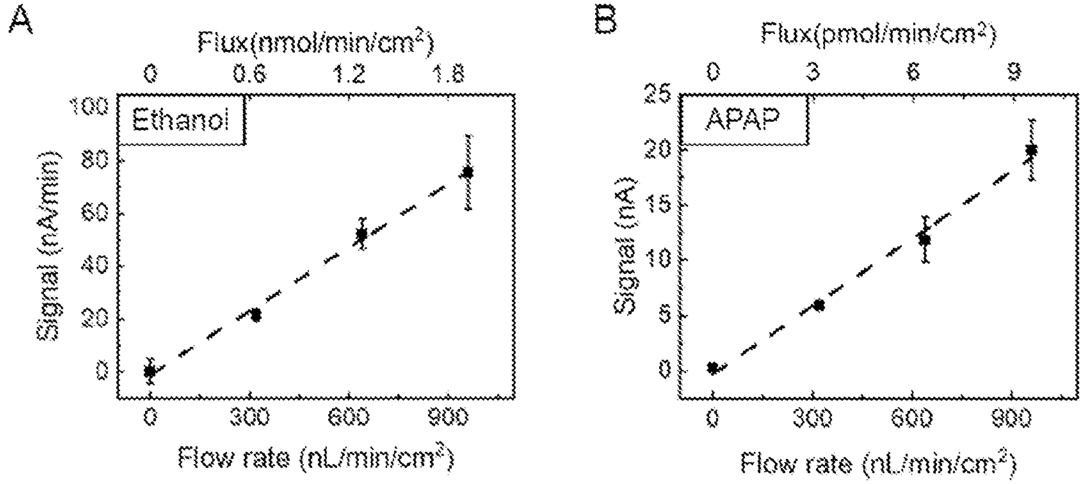
FIGS. 12A and 12B illustrate example aspects of ex-situ TH-sensor characterization under various flow rates according to embodiments.

The characterizations of the two TH-sensors were further extended (using the same setup), by modulating the input flow rate (mimicking the natural perspiration rate variations), while keeping the respective analyte concentration constant. As shown in FIG. 12, for both cases, linear relationships between the measured signals and the corresponding input flow rates were observed. More particularly, FIG. 12 illustrates example aspects of ex-situ TH-sensor characterization under various flow rates according to embodiments. It provides calibration curves of an ethanol TH-sensor (A) and an APAP TH-sensor (B) under various input flow rates (using the artificial fingertip). Error bars indicate standard error (three trials for each target). Ethanol concentration: 2 mM; APAP concentration: 10 μM (both in PBS).

The comprehensive ex-situ sensor characterization results demonstrate that the TH-sensors reliably track the analyte flux (with defined signals being proportional to the analyte flux). These results inform the suitability of the TH-sensors toward retrieving the target biochemical indices at the point of contact with the fingertip.

Development and Validation of the Multimodal Data Acquisition and Processing Modules To acquire the users' biochemical, biophysical, and biometric indices (i.e., bio-inputs) and to enable bio-perception/interpretation, developed were dedicated multimodal data acquisition and processing modules. For each of the bio-input modalities, performed were relevant human subject studies to characterize the respective modules and validate their capabilities in terms of rendering physiologically-relevant readouts.

To characterize the biochemical index acquisition/processing modules, first validated were the core in-situ detection capability of the described TH-sensors. For example, FIGS. 3A-3M illustrate example aspects of development of the multimodal data acquisition and processing modules according to embodiments and validation via human subject studies: (A, B) The captured and linear-fitted ethanol TH-sensor readouts from the index fingertip of a subject (entry at t=0 s) before (A) and 60 min after (B) the intake of an alcoholic beverage (~100 mL, 12.5% alcohol). (C) The temporal profile of the ethanol TH-sensor signal (obtained from the index fingertip of a subject) and concurrently measured BAC levels (20 min before, and after an alcoholic beverage intake: ~100 mL, 12.5% alcohol around t=0 min). (D, E) The captured and baseline-fitted APAP TH-sensor readouts from the index fingertip of a subject before (D) and 60 min after (E) the intake of an APAP-based medication (650 mg APAP). (F) The temporal profile of the APAP TH-sensor signal (obtained from the index fingertip of a subject) and concurrently sampled salivary APAP levels (analyzed using liquid chromatography with tandem mass spectrometry, LC-MS/MS) 5 min before, and after an APAP-based medication (650 mg APAP at t=0 min). (G) PPG sensor readouts from the index fingertip of a subject (Top: IR channel, bottom: red channel). (H) HR of five subjects measured by the PPG sensor and a standard pulse oximeter. (I) The temporal profile of the $SpO_2$ level for a breath holding experiment, concurrently measured by the PPG sensor (top panel) and a standard pulse oximeter (bottom panel). The shaded area indicates the period of breath holding. (J) The user identification and biometric-encryption workflow. (K) A representative scanned and processed fingerprint with the extracted minutiae features annotated. (L) The corresponding plot of relative coordinates and local ridge direction of a pair of template and query fingerprints. (M) Schematic of fuzzy vault algorithm for biometric encryption of bio-inputs, leveraging the fingerprint minutiae pattern as the cryptographic key. Left-column images highlight the relevant units of the CB-HMI data acquisition module: a TH-sensor (here, ethanol), a PPG sensor, and a fingerprint scanner.

Figure 3:
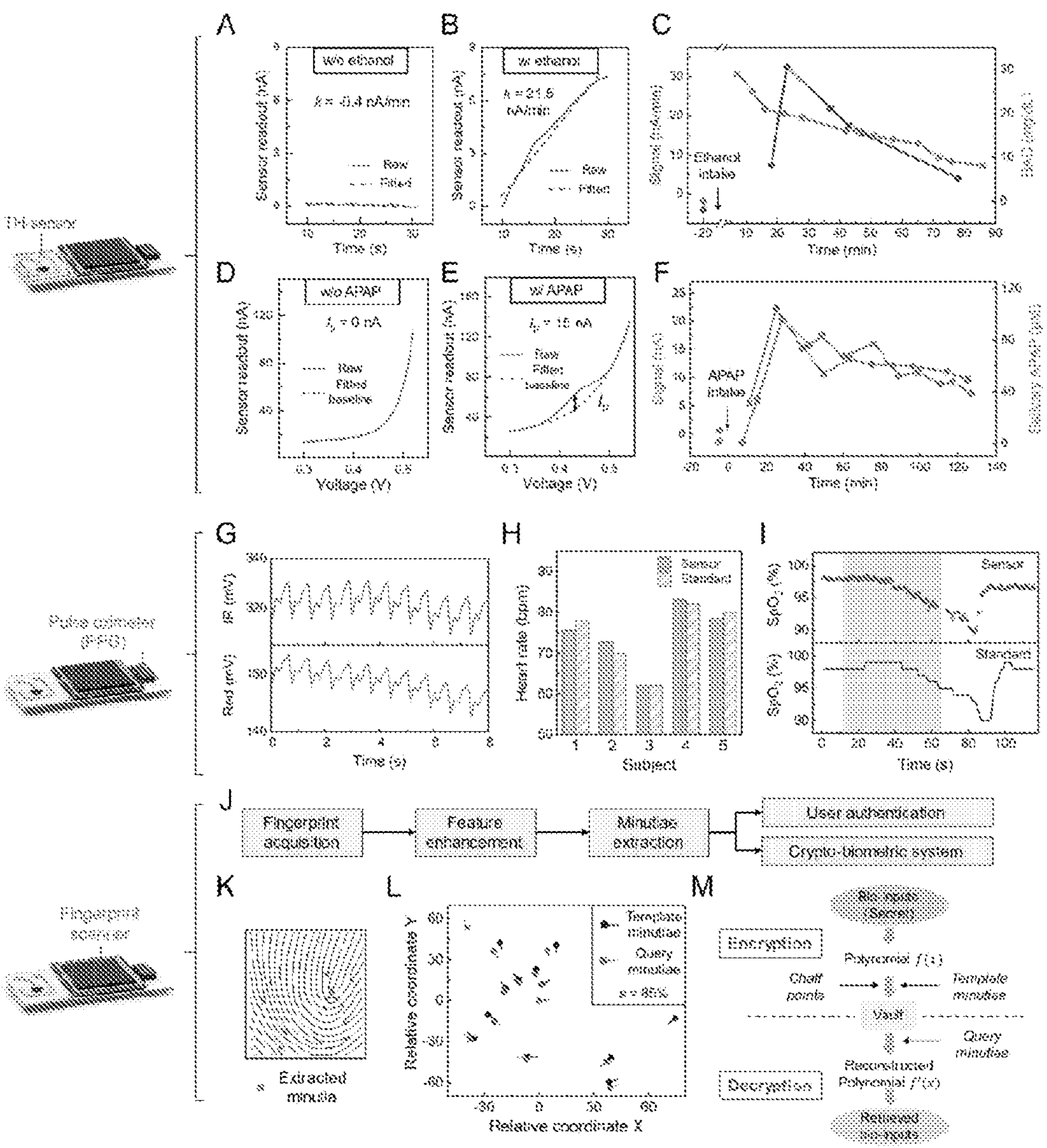
FIGS. 3A to 3M illustrate example aspects of development of the multimodal data acquisition and processing modules according to embodiments and validation via human subject studies.

Embodiments specifically employ the ethanol TH-sensor to assess whether the sensor is capable of differentiating between two states: no alcohol-intake vs. recent intake of an alcoholic beverage. For this context, defined were the measured signal S as the slope of the sensor's amperometric response, and the threshold as Sfree, avg+3×Sfree, SD, where Sfree, avg and Sfree, SD are the average and standard deviation of the signals obtained from the alcohol-free subject (three trials). In these studies, the threshold for determining the alcohol-free state was measured as 0.36 nA/min. Then performed were touch-based TH-sensor measurements before (t=−20 min) and after (t=+60 min) the intake of an alcoholic beverage (~100 mL, 12.5% alcohol). As shown in FIGS. 3A and 3B, the ethanol TH-sensor was capable of differentiating the pre/post-intake events, as evident from the near-zero amperometric current slope for the pre-intake measurement and the relatively steep positive slope in the post-intake measurement (S=21.5 nA/min).

Adopted was a similar study framework to evaluate the in-situ detection capability of APAP TH-sensor. For this context, the measured signal is defined as the voltammetric current peak height (TP), and the threshold for determining the APAP-free state was measured as 3.7 nA (three trials). FIGS. 3D and 3E show the corresponding voltammograms measured by the APAP TH-sensor, 10 min before and 60 min after the intake of an APAP-based medication (containing 650 mg APAP). The comparison of the two voltammograms and the corresponding extracted current peaks (IP, pre-intake ~0 nA vs. IP, post-intake ~15 nA) validates that the developed TH-sensor is capable of detecting the presence of circulating APAP molecules via the devised touch-based modality.

To further illustrate the physiological significance of the biochemical readings obtained from this modality, the study framework was extended to take fingertip-based measurements with a higher temporal resolution and compare the extracted profile with the target molecules' circulating levels. Accordingly, the fingertip-based measurements were performed before and at intermittent time points after the alcoholic beverage/medication intake. To track the molecules' circulating profile, standardized proxy measurements were performed: blood alcohol content (BAC) was estimated using an alcohol breathalyzer and salivary APAP was analyzed with mass spectrometry following our previously reported method (S. Lin, W. Yu, B. Wang, Y. Zhao, K. En, J. Zhu, X. Cheng, C. Zhou, H. Lin, Z. Wang, H. Hojaiji, C. Yeung, C. Milla, R. W. Davis, S. Emaminejad, Noninvasive wearable electroactive pharmaceutical monitoring for personalized therapeutics. Proc. Natl. Acad. Sci. U.S.A. 117, 19017-19025 (2020)).

Figure 13:
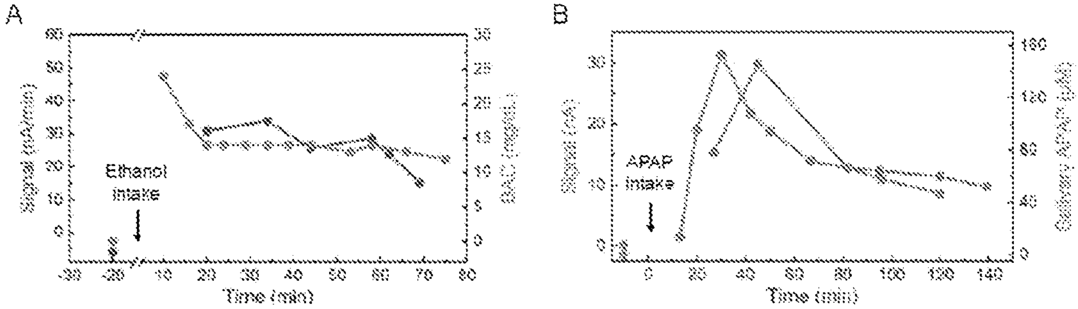
FIGS. 13A and 13B illustrate example aspects of temporal profiles of biochemical indices (second subject) according to embodiments.

As shown in FIGS. 3C and 3F, the temporal profiles of target molecules captured by the TH-sensors closely mirror the molecules' circulating profiles. Similar trend was observed in a second subject following the same study framework. For example, FIG. 13 illustrates example aspects of temporal profiles of biochemical indices (second subject) according to embodiments: (A) The temporal profile of the ethanol TH-sensor signal (obtained from the index fingertip of the second subject) and concurrently measured BAC levels (20 min before, and after an alcoholic beverage intake: ~100 mL, 12.5% alcohol). (B) The temporal profile of the APAP TH-sensor signal (obtained from the index fingertip of the second subject) and concurrently sampled salivary APAP levels (analyzed using LC-MS/MS) 5 min before, and after an APAP-based medication (650 mg APAP).

Furthermore, to verify that the observed trend of the analyte flux is due to the underlying changes in the analyte circulating levels but not the variations in perspiration rate, in a separate study the perspiration rate was monitored intermittently following the same framework and over the same time window. Specifically utilized was a commercially available evaporimeter (Delfin VapoMeter) and a standard temperature probe to directly/indirectly measure the natural perspiration rate profile (J. E. Wingo, D. A. Low, D. M. Keller, R. M. Brothers, M. Shibasaki, C. G. Crandall, Skin blood flow and local temperature independently modify sweat rate during passive heat stress in humans. J. Appl. Physiol. 109, 1301-1306 (2010)).

Figure 14:
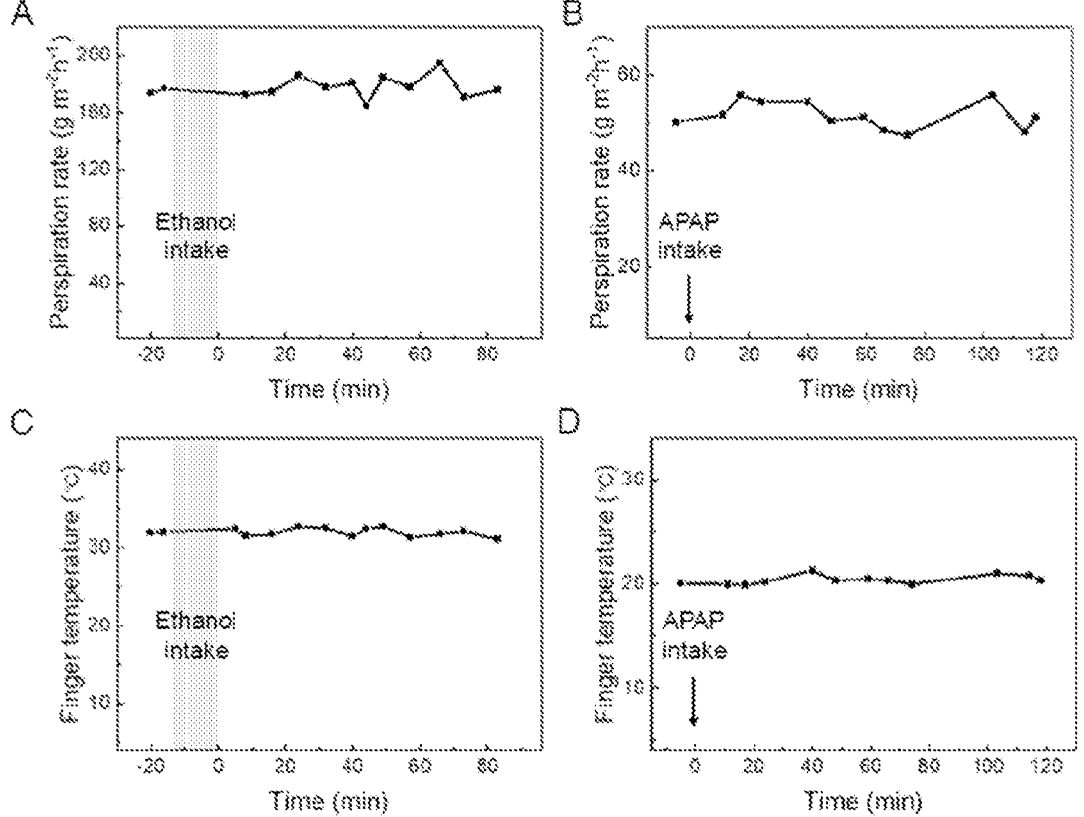
FIGS. 14A to 14D illustrate example aspects of direct and indirect measurement of the natural perspiration rate profile according to embodiments.

As shown in FIG. 14, all the measurements presented relatively stable profiles, indicating that the perspiration characteristic was relatively consistent in the context of the present study. More particularly, FIG. 14 illustrates example aspects of direct and indirect measurement of the natural perspiration rate profile according to embodiments: (A, B) The temporal profile of the thermoregulatory natural perspiration rate (A) and the skin temperature (B) measured on the index fingertip of a subject (before and after an alcoholic beverage intake: ~100 mL, 12.5% alcohol). (C, D) The temporal profile of the thermoregulatory natural perspiration rate (C) and the skin temperature (D) measured on the index fingertip of a subject (before and after an APAP-based medication intake: 650 mg APAP).

To render biophysical index acquisition and processing, embodiments implement a PPG-based sensing interface and the associated inference algorithms to derive the underlying physiological signals such as HR and $SpO_2$. Here, PPG was specifically selected, because of its established clinical utility in assessing the user's overall physiological status (e.g., cardiovascular health and respiration), and its non-invasive and touch-based nature (inline with our envisioned interaction modality) (E. Mohamed, On the analysis of fingertip photoplethysmogram signals. Curr. Cardiol. Rev. 8, 14-25 (2012)). The PPG sensor consists of a red and an infrared (IR) light-emitting diode (with corresponding wavelengths of 660 nm and 880 nm), as well as a photodiode to detect the tissue-reflected light.

FIG. 3G shows representative real-time sensor readouts of the red and IR channels acquired from the fingertip of a subject. To derive the HR information, the pulsing frequency of the measured photoplethysmogram is first extracted by applying a peak identification algorithm. To validate the accuracy of the acquired HR, the processed sensor readouts from five subjects were compared with their corresponding HR obtained by a standard pulse oximeter. As illustrated in FIG. 3H, the two measurement sets are closely matched (difference <3 beats per minute, bpm). Moreover, the ratio of the normalized red and IR readings (Rred/IR) were used to derive the $SpO_2$ information. In order to calibrate the readouts and validate the utility of the sensing module in capturing the $SpO_2$ temporal profile, a breath holding experiment was performed to induce variations in $SpO_2$, following a previously reported protocol (W. G. Zijlstra, A. Buursma, W. P. Meeuwsen-van der Roest, Absorption spectra of human fetal and adult oxyhemoglobin, de-oxyhemoglobin, carboxyhemoglobin, and methemoglobin. Clin. Chem. 37, 1633-1638 (1991)). In this context, $SpO_2$ data was acquired continuously on two fingertips using the corresponding devised acquisition/processing modules and a standard oximeter. As shown in FIG. 3I, as acquired by both methods, the holding of the breath led to a significant $SpO_2$ drop, followed by a rapid increase back to the normal value.

Collectively, the results illustrate the physiological significance of the acquired biochemical and biophysical indices. To seamlessly associate these bio-inputs to the user, while preserving the user's privacy, developed was a built-in user identification/data encryption scheme. This scheme capitalizes on the unique biometric feature of the fingerprint, which is inherently accessible in our envisioned HMI. Accordingly, embodiments implement a fingerprint scanner and developed dedicated image processing algorithms to identify the user and biometrically encrypt the data based on the scanned fingerprint (FIG. 3J). In one example image processing approach, the unique minutiae pattern is extracted from the scanned fingerprint by applying feature enhancement and extraction algorithms (FIG. 3K). The extracted minutiae features are described by their x-coordinate, y-coordinate, and local ridge direction attributes (A. K. Jain, J. Feng, K. Nandakumar, Fingerprint matching. Computer. 43, 36-44 (2010)). To identify the query fingerprint, its minutiae features are compared with those of the template fingerprint (FIG. 3L). In this context, their degree of similarity (s) can be described as:

$$s = \max i\{nmatch\}\sqrt{nquery \cdot ntemplate} \times 100\%$$

where nmatch, nquery, and ntemplate correspond to the number of matched-, query-, and template minutia, respectively for a given query-template minutiae pairing permutation i. Here, define the threshold of 50% for s, as the criterion to determine that any two fingerprints are matched (T. Dunstone, N. Yager, Eds., "Biometric matching basics" in Biometric system and data analysis: design, evaluation, and data mining (Springer, Boston, MA, 2009), pp. 27-43).

The collected biometric index is further utilized to realize a crypto-biometric system (CBS), which encrypts the secret (here, bio-inputs) using a biometric key generated from the minutiae pattern. To this end, embodiments adopt a fuzzy vault scheme (FIG. 3M) that is particularly suitable for the construction of fingerprint-based CBS as it can tolerate the fuzziness inherent to the biometric entries (i.e., input-to-input variations of the minutiae features for the same user) (U. Uludag, S. Pankanti, A. K. Jain, in Audio- and Video-Based Biometric Person Authentication, T. Kanade, A. Jain, N. K. Ratha, Eds. (Springer, Berlin, Heidelberg, 2005), Lecture Notes in Computer Science, pp. 310-319). In short, the bio-inputs are encrypted in a vault using the minutiae-generated key A, which can be decrypted by query minutiae-generated key B only if B overlaps with A substantially (i.e., the two fingerprints are from the same individual).

Figure 15:
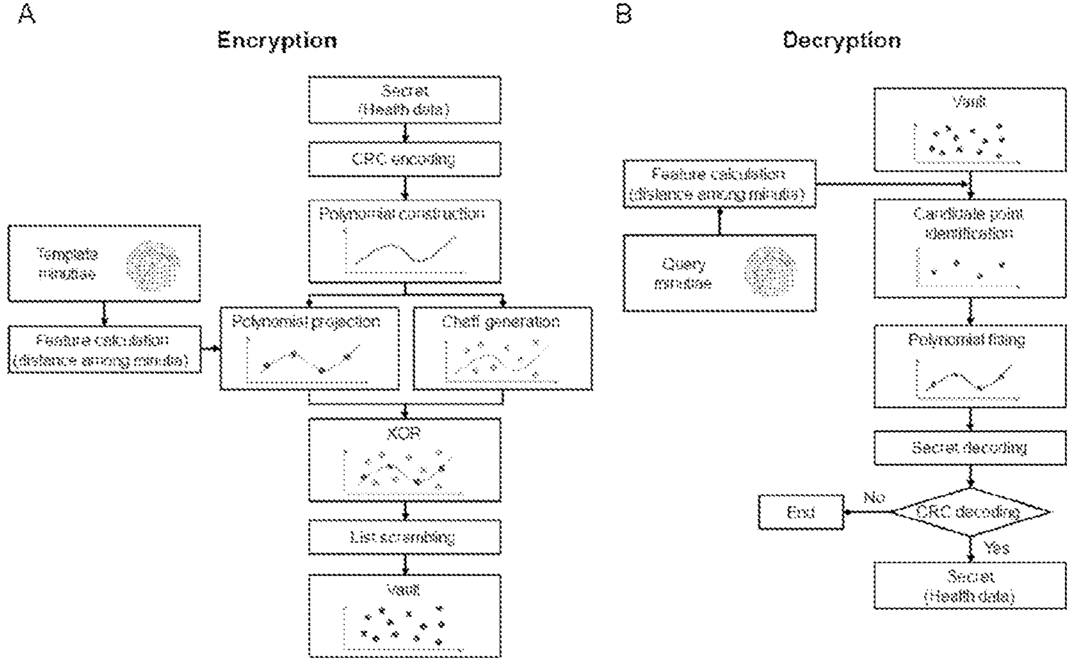
FIGS. 15A and 15B are flowcharts illustrating example aspects of CBS encryption and decryption procedure according to embodiments.

FIG. 15 illustrates example aspects of CBS encryption and decryption procedure according to embodiments: Flow charts of encryption (A) and decryption (B) procedure for the implemented fuzzy vault CBS algorithm. Detailed encryption and decryption procedure is described in the Materials and Method section. XOR: "exclusive of" logical operation.

As shown in FIG. 15A, this encryption process involves: 1) transformation of the bio-inputs into the coefficients of a polynomial equation; 2) projection of the fingerprint minutiae (here, distances among minutiae) onto the polynomial equation to create genuine points; 3) generation of polynomial-offset chaff points; and 3) creation of the vault list using the scrambled genuine points and chaff points. FIG. 15B illustrates the corresponding decryption process. This process involves identifying the genuine points using the query minutiae feature and polynomial fitting to extract the coefficients, followed by reconstructing the bio-inputs.

Furthermore, FIG. 16 shows the application of the implemented CBS given a hypothetical input, illustrating that the input is successfully encrypted/decrypted. More particularly, FIG. 16 illustrates example aspects of biometric-encryption/decryption of a hypothetical input according to embodiments. Tables show the encryption and four decryption attempts: the first two by the genuine subject, and the latter two (outlined in orange) by other subjects. Hypothetical input used: "1234567890"; Calculated CRC digit: 6 (in red). The first column shows the raw scanned fingerprints. The second column shows the processed fingerprints with the extracted minutiae features annotated. The third column shows the calculated biometric keys.

Development and Application of a CB-HMI-Enabled In-Vehicle Safety System

Figure 17:
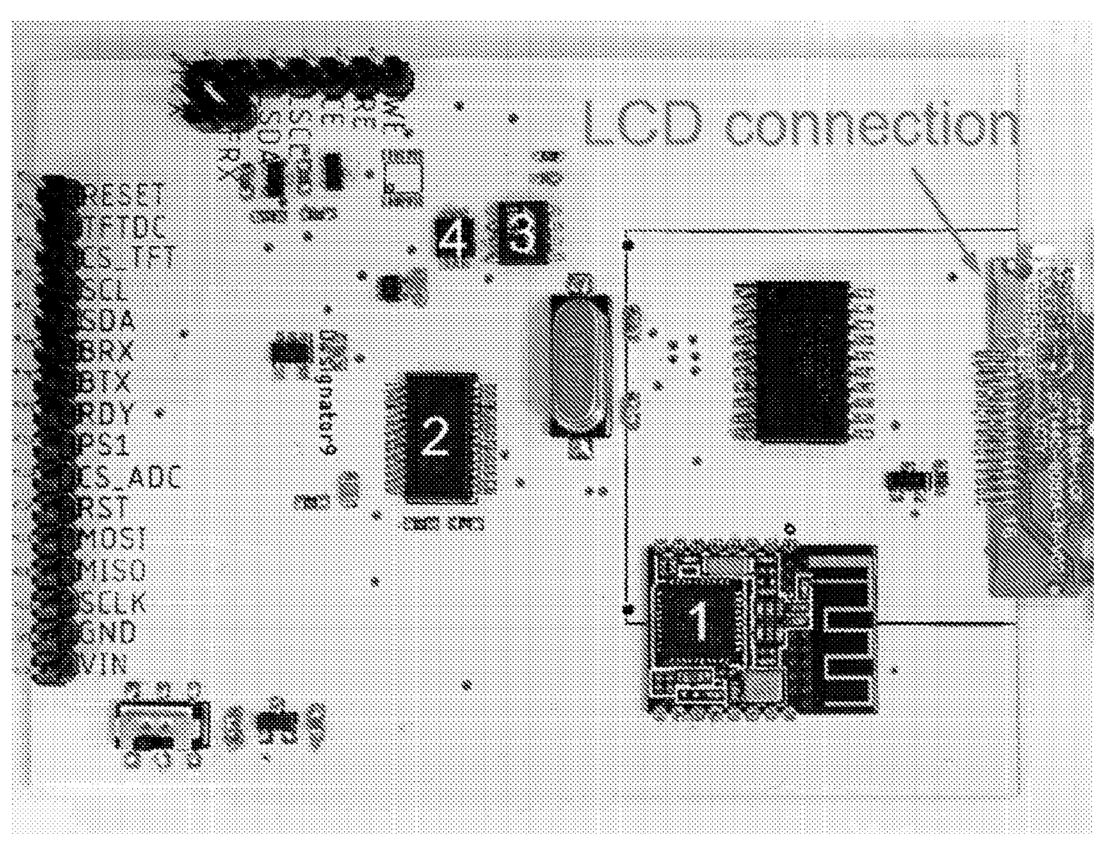
FIG. 17 is a photo illustrating an example data acquisition PCB module according to embodiments.
Figure 18:
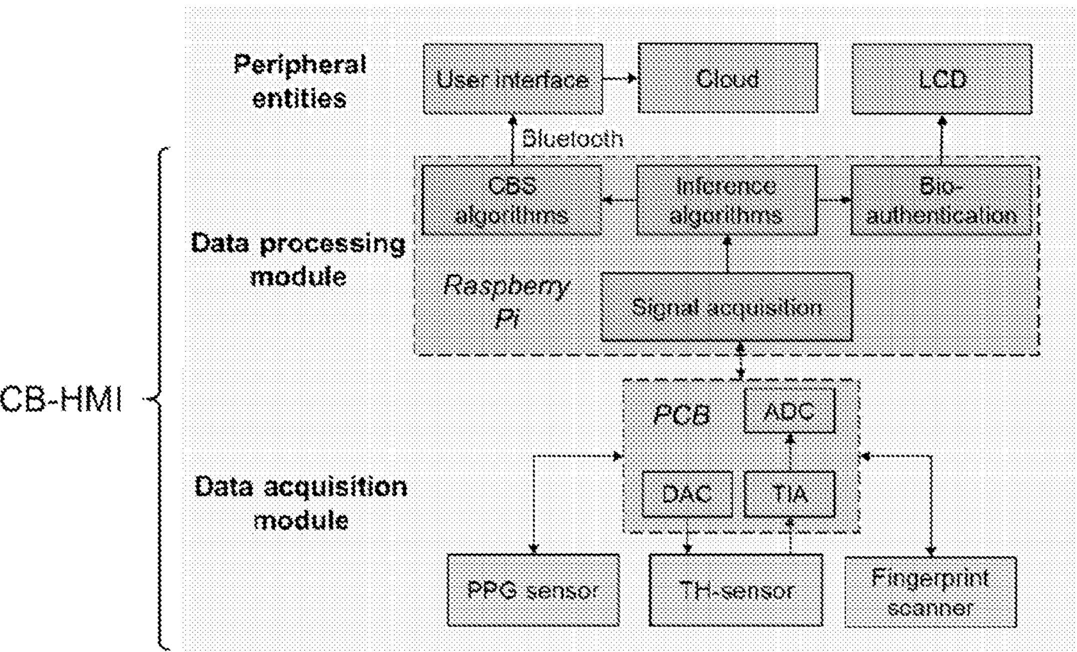
FIG. 18 is a system-level block diagram illustrating an example CB-HMI-enabled system according to embodiments.

The validated acquisition/processing modules for the bio-inputs of interest are integrated within an embedded system to realize the envisioned multimodal CB-HMI. The multimodal CB-HMI can be augmented with other entities (e.g., robotic systems, cloud servers) to facilitate feedback and data storage. For example, FIG. 17 illustrates an example photo of an example data acquisition PCB module according to embodiments. The data acquisition PCB module (secondary) integrates: 1) a Bluetooth module, 2) an ADC, 3) a TIA, 4) a DAC. FIG. 18 illustrates an example system-level block diagram of a CB-HMI-enabled system according to embodiments.

Figure 4:
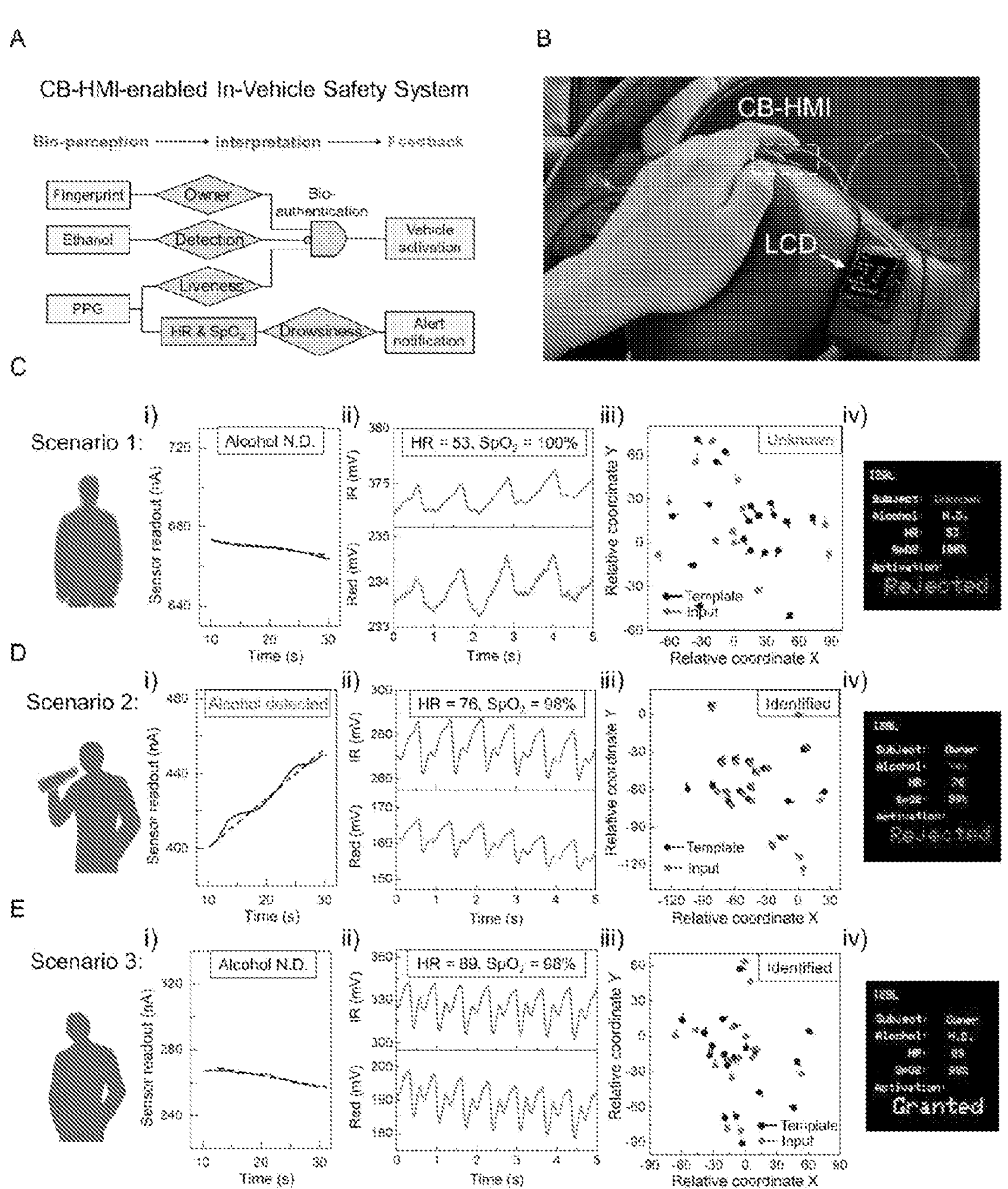
FIGS. 4A to 4E illustrates example aspects of a CB-HMI-enabled in-vehicle safety system according to embodiments.

To demonstrate its utility in a vehicle environment (integral part of our daily experience), first integrated was the CB-HMI on a steering wheel to form an in-vehicle interactive system towards improving driving safety. FIG. 4 illustrates example aspects of a CB-HMI-enabled in-vehicle safety system according to embodiments: (A) Operational workflow of the in-vehicle system. (B) Optical image of the in-vehicle system mounted on a steering wheel, illustrating the envisioned setting. (C-E) Validation of the system functionality in three hypothetical scenarios: non-owner/alcohol-free (C), owner with a recent alcohol intake (D, 1 h before fingertip-entry, ~100 mL beverage containing 12.5% alcohol), and owner/alcohol-free (E). For each scenario: (i) the raw and processed ethanol TH-sensor readouts (upon a fingertip-based entry at t=0 s); (ii) PPG sensor readouts (IR and red channels); (iii) plot of relative coordinates and local ridge direction of the corresponding template and query fingerprints; and (iv) visual feedback to the user via an LCD, displaying: the determined alcohol state of the subject, the derived HR and $SpO_2$ information, and the concluded bio-authentication status. N.D. indicates no detection of alcohol.

Figure 19:
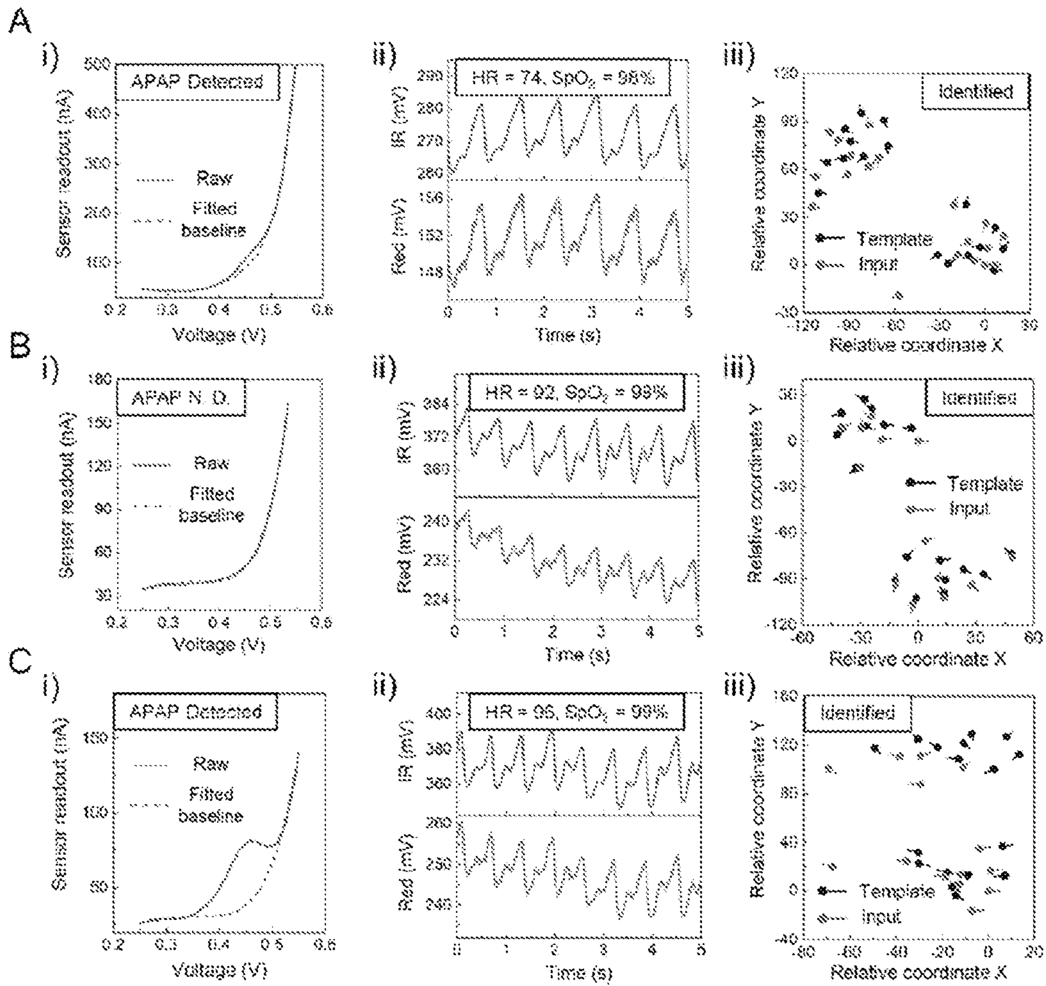
FIGS. 19A to 19C illustrate example aspects of the raw and processed bio-inputs in the medication dispensing study according to embodiments.

FIG. 19 illustrates example aspects of the raw and processed bio-inputs in the medication dispensing study according to embodiments. The raw and processed bio-inputs for three entries at different time points: (A) t=0 h; (B) t=+5 h; (C) t=+6 h. For each entry: (i) the raw and processed APAP TH-sensor readouts (30 s after the fingertip-based entry); (ii) PPG sensor readouts (IR and red channels); and (iii) plot of relative coordinates and local ridge direction of the corresponding template and query fingerprints. N.D. indicates no detection of APAP.

Enabled by the CB-HMI, the system can perceive the driver's ethanol level (using the ethanol TH-sensor), fingerprint, and PPG signal. These degrees of bio-perception can be leveraged to bio-authenticate the drivers (interpretation) for vehicle activation (feedback). For bio-authentication, the system utilizes the bio-input entries to verify the driver's alcohol-free state, biometric match, and liveness of the biometric input (to avoid tampering, by exploiting the PPG signal as a liveness indicator (E. M. Nowara, A. Sabharwal, A. Veeraraghavan, in 2017 12th IEEE International Conference on Automatic Face Gesture Recognition (FG 2017) 56-62 (2017))). Also applicable to this example setting, the derived HR and $SpO_2$ information from the PPG measurements can serve as useful feedback to the driver, as they are informative measures of potential drowsiness (G.-S. Ryu, J. You, V. Kostianovskii, E.-B. Lee, Y. Kim, C. Park, Y.-Y. Noh, Flexible and printed PPG sensors for estimation of drowsiness. IEEE Trans. Electron Devices. 65, 2997-3004 (2018)). As a proof-of-concept, here the authentication status, together with the acquired indices, are transmitted and displayed on a steering wheel-mounted LCD screen to provide visual feedback.

To demonstrate the bio-authentication function of the developed in-vehicle interactive system, the system was tested in three hypothetical scenarios. For each scenario, upon finger pressing, the ethanol readout, the PPG readout, and the fingerprint readout were acquired by the CB-HMI and the feedback information was communicated to the user via an LCD. FIGS. 4C-4E shows the input status, the raw and interpreted bio-inputs (recorded and processed by the integrated modules), together with the generated feedback for each of the scenarios. In the first scenario (FIG. 4C), while the presence of alcohol in the subject's system was not detected (k<0.36 nA/min), the activation request was rejected since the query fingerprint did not match the template of the vehicle owner (s<50%). In the second scenario (FIG. 4D), the activation request was rejected because of the detection of alcohol presence (k>0.36 nA/min) in the driver's circulating system (despite verification of the owner's identity, s>50%). In the last scenario (FIG. 4E), biometric match and alcohol-free readouts were obtained (k<0.36 nA/min, s<50%), and the liveness of the biometric entry was verified, leading to granting the vehicle activation request. For all these scenarios, the system acquired and interpreted the relevant bio-inputs successfully, and identified and communicated the intended course of action correctly.

Development and Application of a CB-HMI-Enabled Medication Dispensing Robotic System To demonstrate the versatility of the CB-HMI and its enabling application, illustrated herein is its utility for assisting the user(s) with their pharmacotherapy regimen. Accordingly, integrated was the CB-HMI into a custom-developed pill case to realize an unprecedented crypto/smart medication dispensing robotic system.

Figure 5:
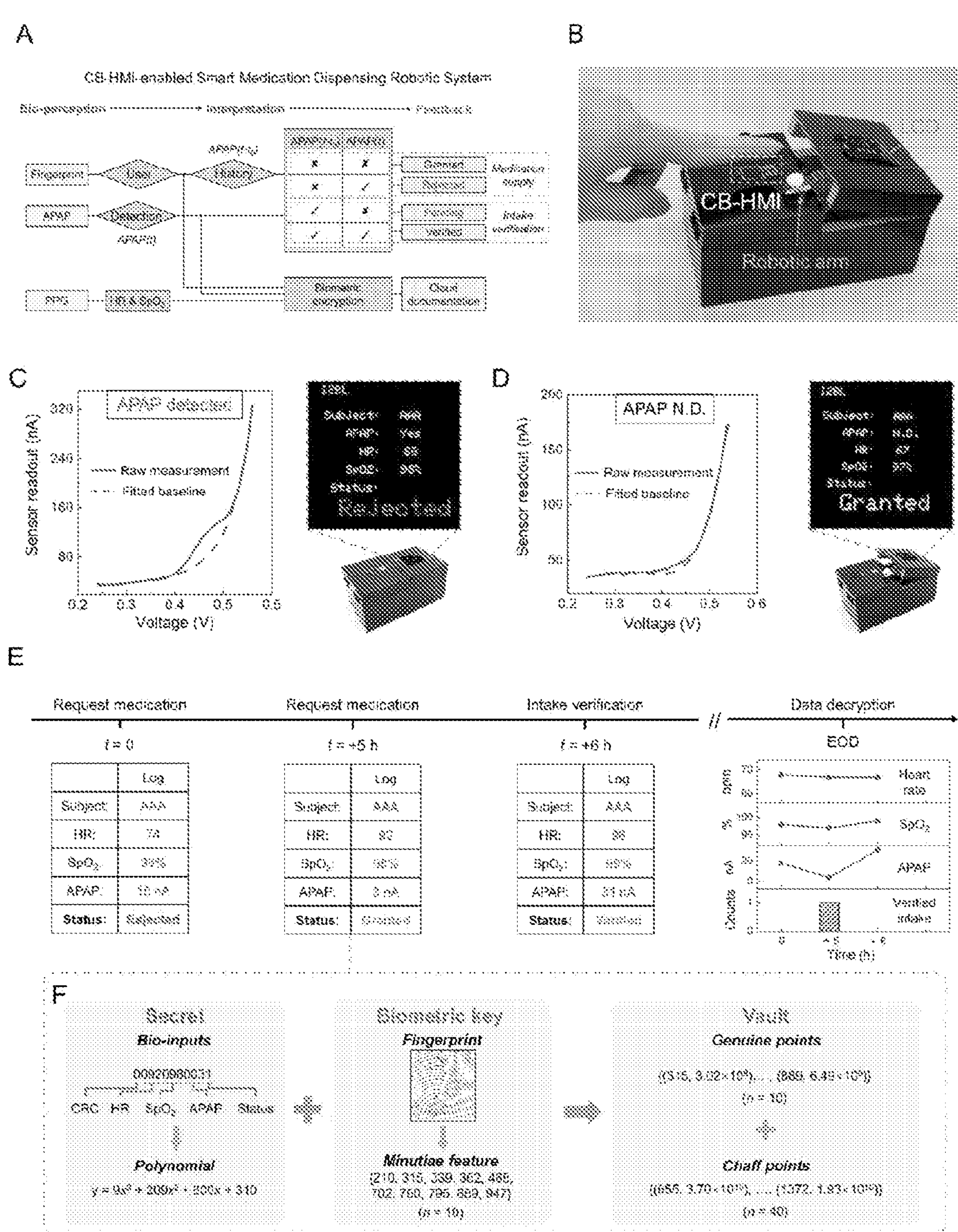
FIGS. 5A to 5F illustrate example aspects of a CB-HMI-enabled medication dispensing robotic system according to embodiments.

FIG. 5 illustrates example aspects of a CB-HMI-enabled medication dispensing robotic system according to embodiments: (A) Operational workflow of the medication dispensing robotic system. t denotes the time of entry and t-t0 represents a 2-h period prior to the time of the entry. "✓" and "X" correspondingly represent the detection of relatively high and low levels of APAP (as determined by the defined signal threshold). (B) Optical image of the fully integrated medication dispensing system consisting of the CB-HMI, a medication delivery robotic arm, medication storage compartment, and an LCD. (C, D) The raw and processed APAP TH-sensor readouts (upon an index fingertip-based entry) and corresponding system response for two cases: a subject with a recent APAP intake (C, 1 h, 650 mg APAP) and an APAP-free subject (D). N.D. indicates no detection of APAP. (E) Acquired bio-inputs and the corresponding status for three index fingertip entries at t=0, +5, and +6 h. Bottom right subfigure tabulates the decrypted retrieved bio-inputs and medication intake status at the end of day (EOD). (F) Encryption procedure for the second entry, illustrating the generation of: i) a secret-embedded polynomial using the acquired bio-inputs; ii) a biometric key based on the extracted minutiae features; and iii) genuine and chaff points to construct the vault.

This system perceives the users' bio-indices, including medication level (here APAP, using the APAP TH-sensor), fingerprint, HR, and $SpO_2$ to bio-authenticate the user (for medication dispensing), verify the medication intake, and update the personal electronic health records.

Specifically, for bio-authentication, the system exploits the bio-inputs to verify the user's identity and no/low medication circulating level as prerequisites for supplying the requested medication. Upon verification, the system dispenses the requested pill with the aid of a robotic arm (mechanical feedback). Similarly, by prompting the user to provide a follow-up touch-based entry, the same bio-inputs can be used to confirm the medication intake (by verifying the elevated circulating level of the medication in tandem with the user's identity). For both situations, the status of the bio-authentication/intake verification, as well as the acquired bio-indices are displayed on a pill case-mounted LCD screen to provide real-time visual feedback to the user. Optionally, this information can be biometrically-encrypted and logged on a cloud-connected server. In this way, the personal electronic health record of the user can be seamlessly updated, while preserving the security of the collected information—all at the point of touch.

FIGS. 5C and 5D demonstrate the bio-authentication function of the developed system for two representative cases: one with a subject with no recent APAP intake (>24 h), the other with the same subject, but with a recent APAP intake (~1 h). In the first case, the medication request was rejected because of the detection of APAP presence at a relatively high level (Ip>3.7 nA, FIG. 5C). In the second case, because no-/minimal circulating drug was detected (Ip<3.7 nA, FIG. 5D), the medication request was granted, triggering the automatic delivery of a single pill by a robotic arm.

To demonstrate all the enabling functionalities of the developed system, it was applied to assist a user under a regular APAP dosing schedule (650 mg every 6 hours). In this illustrative study, three entries were provided by the user at predetermined time points (t=0, +5, and +6 h), where the user had a recent intake (at t=−1 h), which was unbeknownst to the system. FIG. 5E shows the derived status for each entry in relation to the acquired bio-inputs (detailed in FIG. 19): a rejected medication request due to the detection of the presence of relatively high level of APAP (in agreement with the user's APAP intake history); a granted medication request followed by automatic pill delivery (t=+5 h); and a successful intake verification (t=+6 h). For each entry, the acquired bio-inputs were biometrically-encrypted in-situ (using our embedded CBS) and transmitted to a Google cloud server for storage. The description of the encryption process for a representative entry (t=+5 h) is shown in FIG. 5F. At the end of the day, upon the user's request—simply through a fingertip entry—all the stored encrypted electronic medical records were successfully retrieved and decrypted to render the longitudinal profile of the acquired bio-indices.

One example touch-based lithium sensing interface according to embodiments comprises a thin gel (hereinafter, TOH)—which simultaneously serves as a bio-interface to sample the analyte flux from the skin surface and a medium for electrochemical analysis—and a lithium ISE to quantify sampled lithium ions. Here, the two components were first individually developed and characterized.

FIG. 21 illustrates example aspects of characterization of individual components of the sensing interface of these embodiments: (A) Schematics of the TOH fabrication workflow. (B) Normalized TOH weight over 14 days. Error bars indicate standard deviation (n=10). (C) Exploded view of a Li+ ISE (WE: working electrode; RE: reference electrode). (D) Potentiometric readout of a representative Li+ ISE with increasing Li+ (lithium chloride, LiCl) concentration. Inset shows the corresponding calibration plot. Error bars indicate standard deviation of three sensors. The tests were performed in an electrochemical cell containing artificial sweat solution.

The agarose-based TOH was fabricated using a molding technique (FIG. 21A). Central to rendering an anti-dehydration property, the gel solution was prepared in a bi-solvent matrix containing water and glycerol, where hydrogen bonds were formed between water, glycerol, and agarose molecules to "freeze" water molecules within the gel matrix (Boral, S.; Bohidar, H. B. Effect of Water Structure on Gelation of Agar in Glycerol Solutions and Phase Diagram of Agar Organogels. J. Phys. Chem. B 2012, 116 (24), 7113-7121. https://doi.org/10.1021/jp3022024). The as-fabricated organohydrogels were then dried overnight to evaporate unbound, free water molecules, resulting in a TOH with stabilized composition. As shown in FIG. 21B, the fabricated TOHs demonstrated negligible weight loss for a period over two weeks in an ambient environment, illustrating its superior anti-dehydration capability. Moreover, the TOHs have a low thickness of ~60 pm, which will facilitate rapid TOH-sensor response and amplified signal (Lin, S.; Zhu, J.; Yu, W.; Wang, B.; Sabet, K. A.; Zhao, Y.; Cheng, X.; Hojaiji, H.; Lin, H.; Tan, J.; Milla, C.; Davis, R. W.; Emaminejad, S. A Touch-Based Multimodal and Cryptographic Bio-Human-Machine Interface. Proceedings of the National Academy of Sciences 2022, 119 (15), e2201937119. https://doi.org/10.1073/pnas.2201937119).

Figure 24:
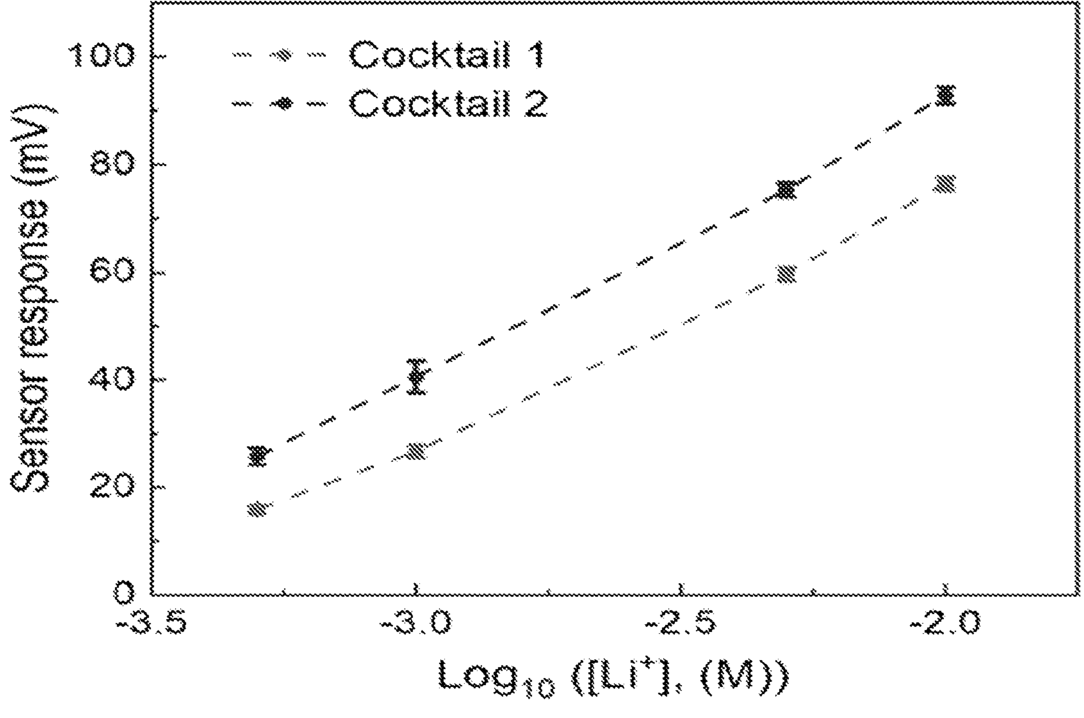
FIG. 24 is a graph illustrating supplemental aspects of embodiments.

The underlying lithium sensing interface was constructed using a solid-contact ISE (FIG. 21C), which consists of: 1) an ion-selective membrane (ISM) serving as the recognition element for selective lithium chemisorption; 2) a poly(3,4-ethylenedioxythiophene) polystyrene sulfonate (PEDOT:PSS)-based ion-to-electron transducer, featuring a large redox capacitance to render low sensor drift; and 3) a gold electrode patterned on a flexible polyethylene terephthalate (PET) substrate. Here, the composition of the ISM cocktail was specifically selected towards optimal performance in a sweat-mimicking matrix (FIG. 24).

Figure 25:
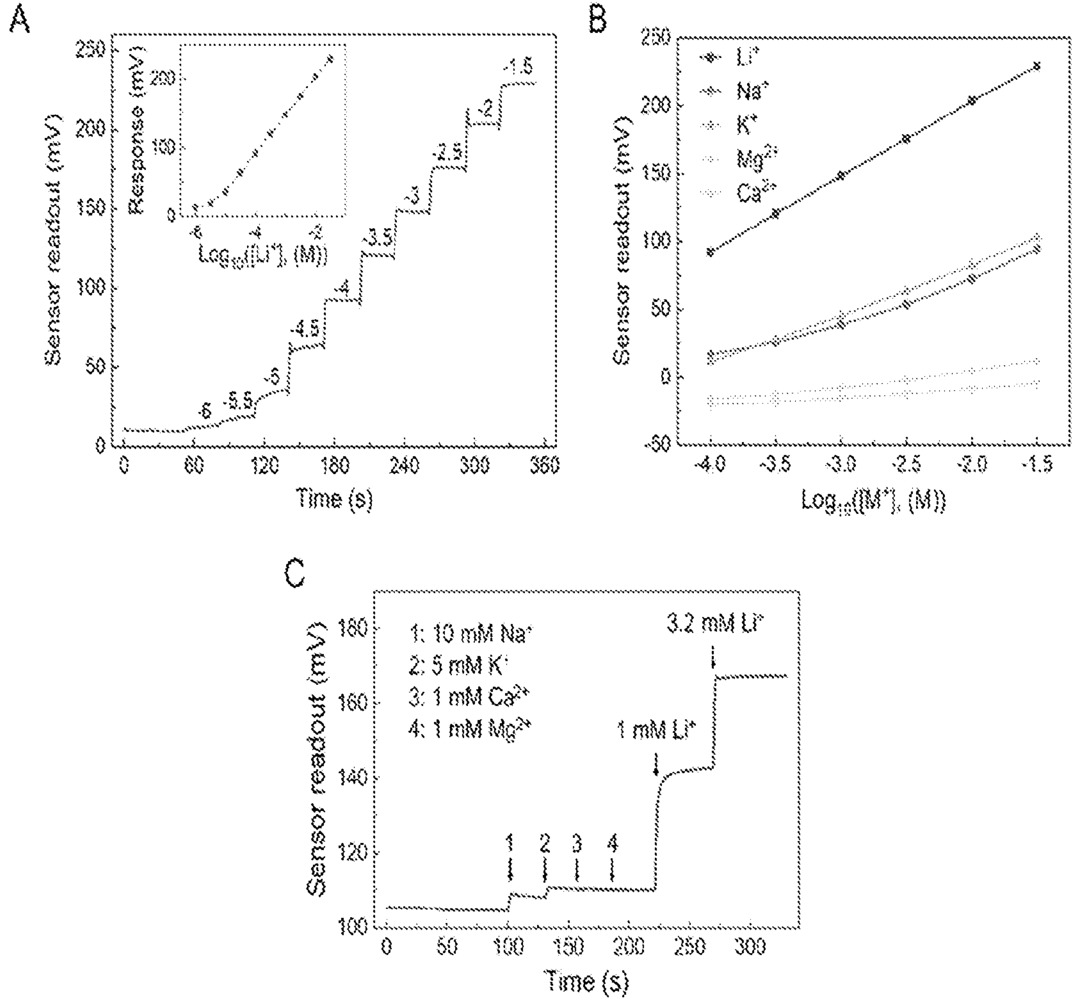
FIGS. 25A to 25C are graphs illustrating supplemental aspects of embodiments.

The developed sensor was first characterized in a standardized matrix. In a deionized water background, the sensor shows a Nernstian response to Li+ within the range of $10^{-5}$-10−1.5 M (FIG. 25A), which is comparable to the previously reported Li+-ISEs (Novell, M.; Guinovart, T.; Blondeau, P.; Xavier Rius, F.; J. Andrade, F. A Paper-Based Potentiometric Cell for Decentralized Monitoring of Li Levels in Whole Blood. Lab on a Chip 2014, 14 (7), 1308-1314. https://doi.org/10.1039/C3LC51098K; and Sweilam, M. N.; Varcoe, J. R.; Crean, C. Fabrication and Optimization of Fiber-Based Lithium Sensor: A Step toward Wearable Sensors for Lithium Drug Monitoring in Interstitial Fluid. ACS Sens. 2018, 3 (9), 1802 1810. https://doi.org/10.1021/acssensors.8b00528). The intrinsic selectivity of the developed sensor was evaluated by testing the sensor in solutions containing either the interfering ions (e.g., Na+, K+, $Ca_2$+, $Mg_2$+) or Lit. As shown in FIG. 25B, the potentials recorded with all the interfering ions were much lower than that of Li+. Selectivity coefficients were not defined because the sensor did not give a Nernstian response to interfering ions (Bakker, E.; Pretsch, E.; Bühlmann, P. Selectivity of Potentiometric Ion Sensors. Anal. Chem. 2000, 72 (6), 1127-1133. https://doi.org/10.1021/ac991146n). More informatively, considering that natural perspiration is the primary source of touch-based sensing, the developed sensor was further characterized in a custom-developed artificial sweat matrix (Wang, B.; Zhao, C.; Wang, Z.; Yang, K.-A.; Cheng, X.; Liu, W.; Yu, W.; Lin, S.; Zhao, Y.; Cheung, K. M.; Lin, H.; Hojaiji, H.; Weiss, P. S.; Stojanović, M. N.; Tomiyama, A. J.; Andrews, A. M.; Emaminejad, S. Wearable Aptamer-Field-Effect Transistor Sensing System for Noninvasive Cortisol Monitoring. Science Advances 2022, 8 (1), eabk0967. https://doi.org/10.1126/sciadv.abk0967), which effectively mimics the ionic environment of sweat. FIG. 21D shows the sensors' response to Li+ in artificial sweat, where a measurable signal to a Li+ concentration as low as $10^{-5}$ M and a linear range slope (m) of 57 mV/dec were observed. Noting that the clinically relevant range of Li+ in non-invasively retrievable biofluid (e.g., saliva) is ~0.5-3 mM (~twice compared to the corresponding serum concentrations) (Shetty, S. J.; Desai, P. B.; Patil, N. M.; Nayak, R. B. Relationship Between Serum Lithium, Salivary Lithium, and Urinary Lithium in Patients on Lithium Therapy. Biol Trace Elem Res 2012, 147 (1), 59-62. https://doi.org/10.1007/s12011-011-9295-3; and Serdarevid, N.; Kozjek, F.; Malešič, I. Saliva And Serum Lithium Monitoring In Hospitalized Patients And Possibility To Replace Serum To Saliva. Bosn J Basic Med Sci 2006, 6 (4), 32-35), the developed sensor is theoretically capable of analyzing a touch-based input in the presence of analyte dilution in TOH. Furthermore, FIG. 25C shows that the sensor's response to the variations of interfering ions was minimal as compared to that of Li+, demonstrating a good selectivity in the envisioned application.

The individually-characterized TOH and lithium ISE were then coupled to form a TOH-ISE sensing interface, where the TOH serves as the sensing medium and ISE readout reflects the lithium level in the TOH.

First characterized was the TOH-ISE's readout stability. In conventional ISE sensing, to realize a low-drift readout, the sensor requires extensive conditioning in a sample-mimicking environment prior to the test, which is operational-complicated and time-consuming (Guzinski, M.; Jarvis, J. M.; Pendley, B. D.; Lindner, E. Equilibration Time of Solid Contact Ion-Selective Electrodes. Anal. Chem. 2015, 87 (13), 6654-6659. https://doi.org/10.1021/acs.analchem.5b00775). In an example TOH-ISE configuration, leveraging the high stability of the TOH, the TOH coating serves as a controlled micro-environment to condition the ISE in-situ. To demonstrate its utility, compared was the TOH-ISEs' readout drift in their as-fabricated state (i.e., right after the coupling of TOHs and ISEs) and in-situ-conditioned state (i.e., after overnight storage in the coupled form).

Figure 22:
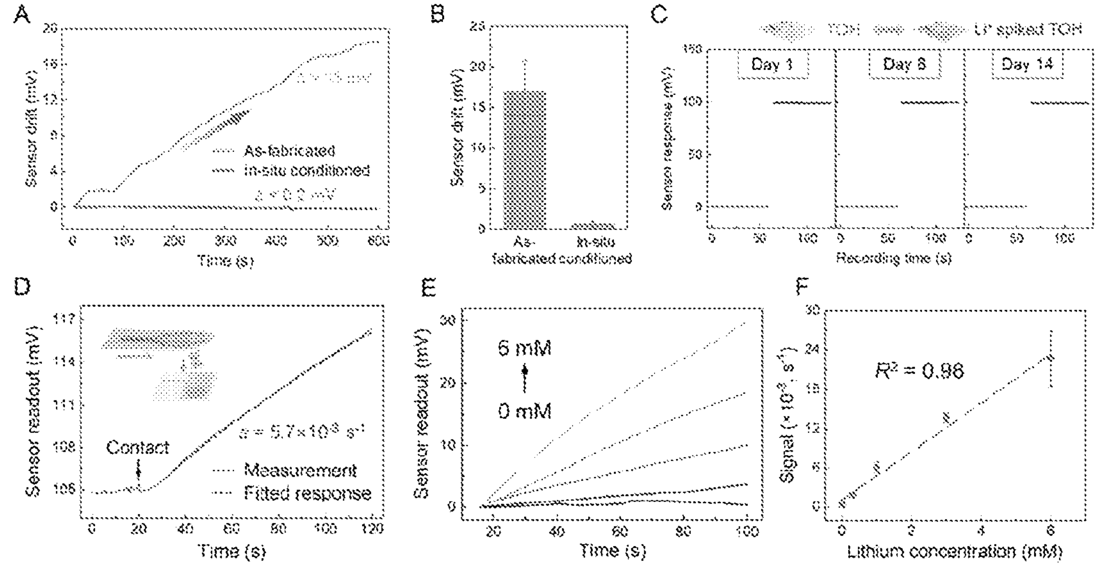
FIGS. 22A to 22F illustrate example aspects of ex-situ TOH-ISE characterization according to embodiments.

FIG. 22 illustrates example aspects of ex-situ TOH-ISE characterization according to embodiments: (A) Real-time potentiometric readout drift of a representative TOH-ISE in its as-fabricated state (right after the coupling of TOH and ISE) and after overnight conditioning (in-situ conditioned state). Inset shows the schematic of a TOH-ISE. (B) Corresponding sensing signal drift magnitude in the first 10 min of the test. Error bars indicate standard deviation (n=5). (C) Potentiometric response of a TOH-ISE interrogated on different days after fabrication. Lithium-spiked TOH (1 mM Li+ in the prepared gel solution) was used to replace the TOH in order to test the response of the interface to lithium. (D) Potentiometric recording of a TOH-ISE upon contact with a microfluidic artificial fingertip (delivering artificial sweat solution with 1 mM Li+). The dotted line shows the corresponding signal interpretation framework fitted readout. Inset shows the schematic of the testing setup. (E) Potentiometric responses of a TOH-ISE to input fluid with various Li+ concentrations (0, 0.3, 1, 6 mM, all post-contact with the artificial fingertip). (F) Corresponding calibration curve. Error bars indicate standard deviation (three trials).

As shown in FIGS. 22A, 22B, the as-fabricated interface drifted significantly, while a small variation was observed in the in-situ conditioned case. The small drift can be attributed to the equilibrium of the functional layers in ISE (e.g., hydration, ion activity in the ISM, PEDOT:PSS redox state) during the conditioning process (Guzinski, M.; Jarvis, J. M.; Perez, F.; Pendley, B. D.; Lindner, E.; De Marco, R.; Crespo, G. A.; Acres, R. G.; Walker, R.; Bishop, J. PEDOT(PSS) as Solid Contact for Ion-Selective Electrodes: The Influence of the PEDOT(PSS) Film Thickness on the Equilibration Times. Anal. Chem. 2017, 89 (6), 3508-3516. https://doi.org/10.1021/acs.analchem.6b04625). Leveraging this feature, the TOH-ISE interface effectively eliminates the time-consuming ISE conditioning step before use each time, rendering a plug-and-sense capability. To illustrate this capability, the developed TOH-ISE was interrogated on different days post fabrication. A lithium-spiked TOH was utilized to probe the interface's lithium response. As shown in FIG. 22C, the interface manifested reproducible lithium responses for two weeks and the sensor readouts were stable for all the measurements.

To deploy TOH-ISE for touch-based sensing, the unique analyte mass transport behavior must be examined in relation to the TOH-ISE readout. Unlike the conventional sample-to-answer biochemical sensing scenarios, in the touch-based sensing, the epidermal influx of the analyte (f) into the gel-based interface dynamically changes the analyte concentration/distribution in the gel. Furthermore, with a low analyte concentration, the non-linearity of the ISE response must be considered, which, together with the logarithmic nature of the ISE response, makes the signal interpretation non-trivial.

To develop an ISE-specific signal interpretation framework for touch-based lithium sensing, one can start by referring to the Nicolsky-Eisenman equation, which empirically describes the ISE readout (EMF) in relation to the ion concentration levels in its surrounding environment (Id.):

$$EMF = \frac{RT}{z_I F}\log\left(a_1 + \sum k_{IJ} a_J^{z_I/z_J}\right) + E_0$$

Figure 26:
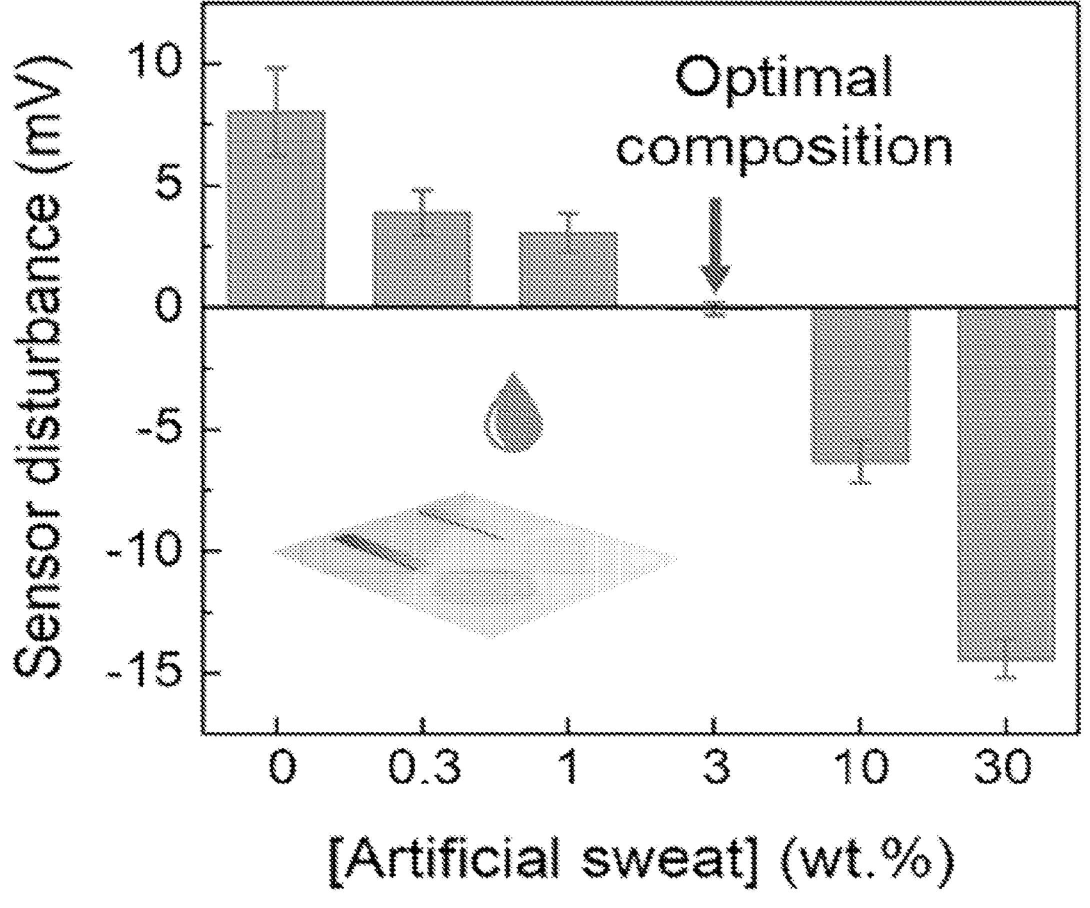
FIG. 26 is a graph illustrating supplemental aspects of embodiments.

Here a and z are the activity and the charge of the target ion (I; in our case Li+) and non-target ion (J), respectively; $K_{IJ}$ is the selectivity coefficient for each interfering ion; E_0 is the standard potential of EMF; and R, T, and F represent the universal gas constant, the absolute temperature, and the Faraday constant, respectively. For a touch-based lithium input, $a_i$ gradually increases due to the epidermal analyte influx ($a_i$=f*t), while the concentration variations of non-target ions have minimal influence on the readout. The latter part is achieved by optimizing the ionic composition of the TOH (FIG. 26). Accordingly, the dynamic sensor readout as be presented as:

$$EMF(t) = \frac{RT}{z_I F}\log\left(f_t \cdot t + \sum k_{IJ} a_J^{\frac{z_I}{z_J}}\right) + E_0 = m \cdot \log(s \cdot t + 1) + E_0'(2)$$

To this end, the sensing signal (s, proportional to analyte flux) can be extracted by fitting the TOH-ISE readout into the equation above.

Figure 27:
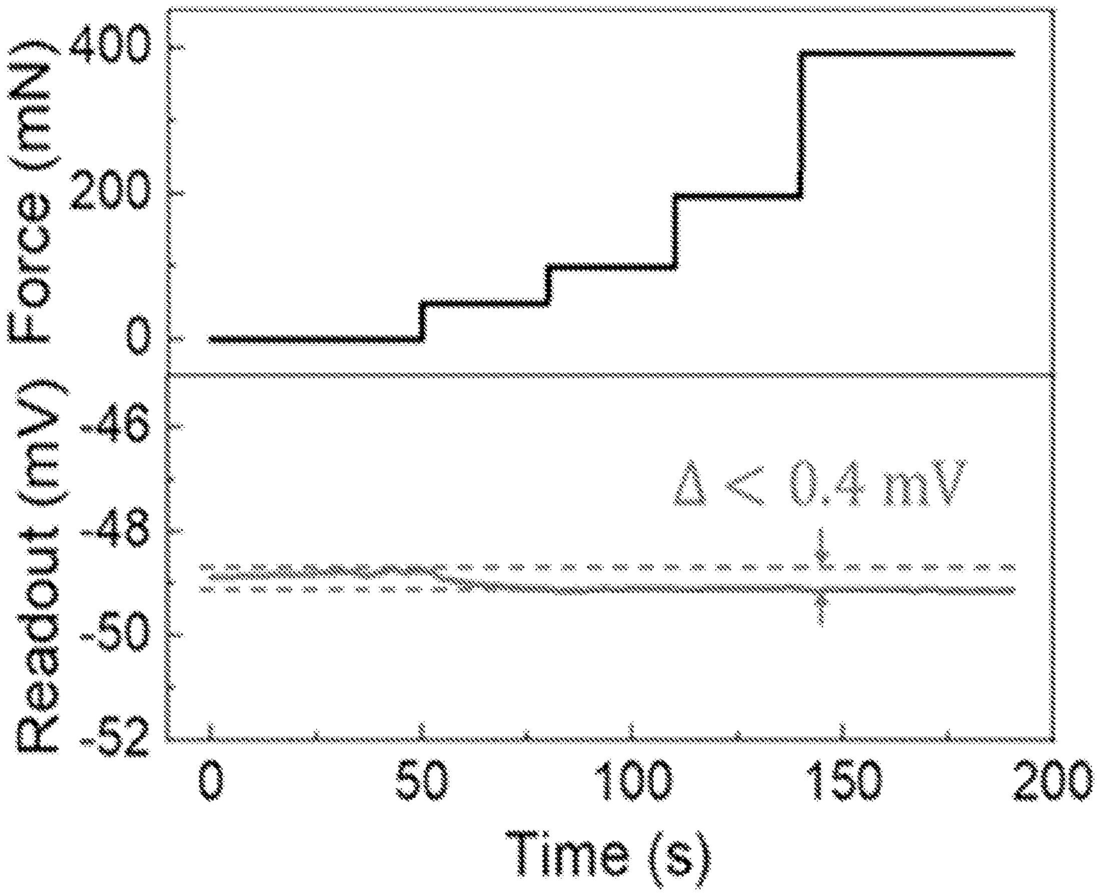
FIG. 27 is a graph illustrating supplemental aspects of embodiments.

To validate the TOH-ISE interface and signal interpretation framework, coupled was the TOH-ISE with a previously developed microfluidic artificial fingertip setup, which mimics a skin surface that continuously delivers analytes onto the sensing interface (Id.). As shown in FIG. 22D, upon lithium introduction, the sensor readout gradually increased, which reflected the introduced lithium flux. The introduced lithium concentrations were modulated to model the variation of circulating lithium levels. FIGS. 22E and 22F show the real-time potentiometric readouts and the corresponding sensing signal (extracted via the interpretation framework above). The high-level of correlation (R2=0.98) demonstrates the suitability of the devised approach for touch-based lithium analysis. Relevant to the touch-based sensing context, we also investigated the influence of the pressing force variability on the TOH-ISE readout. FIG. 27 shows that mounting weights on the TOH-ISE did not cause sensor readout change, which is primarily due to the minimal electron motion involvement in the case of potentiometric sensing.

Further validated was the performance of the developed TOH-ISE in an in-situ lithium adherence monitoring study. To this end, a subject prescribed lithium-based medication was recruited. Touch-based sensing using the TOH-ISE interface was performed before and after the scheduled drug intake (900 mg lithium carbonate): ~0-1 h pre-intake and ~1-2 h post-intake. To demonstrate the physiological significance of the touch-based readouts, saliva samples were collected at the same time with touch-based sensing, and analyzed using a standard colorimetric assay subsequently. The choice of saliva was motivated by lithium's reported saliva-blood correlation as well as the similar analyte partitioning pathway of sweat and saliva (Id). In a control experiment, touch-based sensing and salivary lithium analysis were also performed on three healthy subjects, where circulating lithium is expected to be negligible.

Figure 23:
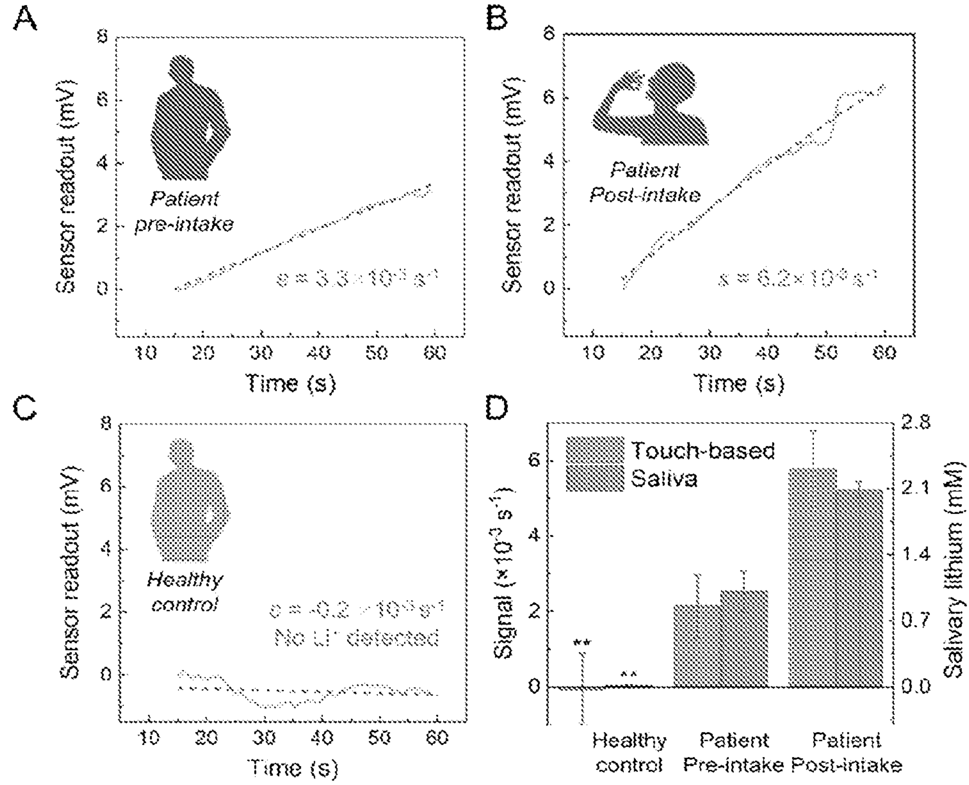
FIGS. 23A to 23D illustrate example aspects of in-situ TOH-ISE validation according to embodiments.

FIG. 23 illustrates example aspects of in-situ TOH-ISE validation according to embodiments: (A-C) Potentiometric TOH-ISE readouts and fitted responses on a patient before (A) and after (B) the scheduled daily lithium-based medication intake (900 mg lithium carbonate) as well as a healthy control subject (C). (D) Healthy control's touch-based sensing signal and salivary lithium concentration versus the patient's measurements illustrating the negligible lithium concentrations in both measurements for the healthy control. **$P<0.01$ versus patients' measurements. Error bars indicate standard deviation. Healthy control: three subjects; Patient: three trials on the same subject.

FIGS. 23A-23C show the representative raw and fitted TOH-ISE readouts from the three scenarios. From the patient inputs, a larger signal was obtained post drug intake as compared to the pre-intake case, inferring an elevated circulating lithium level. On the other hand, a near-zero signal was recorded from the healthy subject. FIG. 23D shows the collective TOH-ISE readouts and the corresponding saliva lithium levels, where the observed similar trend demonstrates the potential utility of the touch-based non-invasive sensing for direct drug adherence monitoring application.

Discussion

Embodiments provide an HMI modality—with built-in cryptographic multimodal bio-perception and interpretation capabilities—that translates the user's touch-based entries into encrypted biochemical, biophysical, and biometric indices.

As its central component, one example HMI (termed CB-HMI) features a TH-coated sensing interface to non-invasively and inconspicuously measure biochemical indices. The employed TH-sensing methodology bypasses the fundamental challenge of circulating analyte accessibility (posed by the skin's barrier function), enabling the perception of body's chemistry at molecular levels. Embodiments include specifically developed TH-sensors and defined signal terms to track the on-skin flux of circulating ethanol and APAP molecules. Using a custom-developed microfluidic artificial fingertip, characterized and validated were the TH-sensors' responses ex-situ. The artificial fingertip configuration could be generally helpful in catalyzing the future sensor development efforts: it provides an accessible and controlled setup to study the effect of analyte partitioning parameters (e.g., original concentration and flux) and confounding factors (e.g., the mechanical force exerted by finger pressing) on the sensor's response.

Expanding the scope of the biological perception, the CB-HMI additionally features physical sensors (PPG and fingerprint scanner) to acquire the user's biophysical (HR, $SpO_2$) and biometric (fingerprint minutiae pattern) indices. Upon integrating the associated data acquisition and processing modules, we validated the CB-HMI's complete bio-perception/interpretation functionality via human subject studies. Collectively, the results demonstrated the CB-HMI's capabilities in terms of acquiring physiologically-relevant readouts of target bio-indices, as well as user-identifying and biometrically-encrypting these indices in-situ.

Furthermore, by upgrading the common surrounding objects with the CB-HMI, and subsequently, equipping them with biological perception/interpretation, embodiments create new interactive solutions to promote the user's quality of life. The demonstrated interactive system for vehicle activation, which is capable of detecting the circulating alcohol level at well below the legal limit for driving (National Highway Traffic Safety Administration, "Digest of impaired driving and selected beverage control laws, thirtieth edition, current as of Dec. 31, 2015" (DOT HS 812 394, U.S. Department of Transportation, Washington, D C., 2017)), could be particularly helpful in preventing DUI—one of our modern societal challenges claiming >10,000 lives each year in the United States alone (National Highway Traffic Safety Administration, "Overview of the 2019 crash investigation sampling system" (DOT HS 813 038, U.S. Department of Transportation, Washington, D C., 2020), p. 5). The demonstrated crypto-smart medication dispensing robotic system could serve as an ideal drug adherence monitoring solution, owing to its built-in user bio-authentication, medication intake verification, and seamless electronic medical record keeping capabilities (W. Y. Lam, P. Fresco, Medication Adherence Measures: An Overview. Biomed Res. Int. 2015, e217047 (2015)). The demonstrated biochemical sensing capabilities can be extended to target other medications and substances and augmented with advanced algorithms to determine appropriate drug dosing and cut-off values. The acquired insight can be further enriched and contextualized by incorporating a dedicated interface for logging user reported symptoms. Moreover, the feedback functionality could also be extended to alert the subject of dose due/overdue. In this way, the present technology can be positioned to address one of our societal grand healthcare challenges: non-optimized medication therapy, which is fueled by inappropriate dosing and patients' poor medication adherence, and results in 275,000 deaths and $530B in healthcare costs, annually (J. H. Watanabe, T. McInnis, J. D. Hirsch, Cost of prescription drug-related morbidity and mortality. Ann. Pharmacother. 52, 829-837 (2018)).

Toward providing a comprehensive bio-perception of the user, the devised HMI can be adapted to acquire a wider panel of psychological and physiological indices. For example, the presented TH-based sensing methodology can be applied to target endogenous molecular indicators of health, including hormones, nutrients, metabolites, and cytokines. To interpret these measurements and to inform actionable feedback, the influence of various confounding factors (e.g., skin and gland metabolism, perspiration rate variation) needs to be carefully characterized (via large-scale clinical studies), and if necessary mitigated (via engineering solutions and machine learning algorithms). To this end, the incorporation of auxiliary sensors (e.g., temperature, humidity) could be helpful to standardize the measurements and to account for underlying sources of inter-/intra-individual variability. Furthermore, the presented PPG-based sensing modality can be extended to derive other informative biophysical indices such as respiratory rate and blood pressure.

The unique built-in data encryption feature of the present HMI inherently provides the layer of security necessary to protect such wealth of personal information, while enabling decentralized bio-data collection and processing within Internet of Things and blockchain infrastructures. To this end, dedicated CBS optimization/validation efforts are required to improve the biometric encryption algorithm's reliability (e.g., via development of advanced key generation algorithms and validation with standard databases).

Ultimately, the maturity and proliferation of the CB-HMI, together with other classes of intelligent HMIs, will equip our surroundings with a comprehensive and deep awareness of the individuals' psychophysiological state and needs. This advancement will seed the foundation for creating interactive and adaptive environments to actively assist the users in reaching their optimal outcomes efficiently.

Moreover, additional or alternative embodiments described herein relate to a touch-based lithium sensing interface, which consists of a thin organohydrogel and a lithium ion-selective electrode (ISE). The devised sensing interface uniquely features a highly-stable "plug-and-sense" operation, which is enabled by the gel's anti-dehydration property (provided by the bi-solvent matrix) and the in-situ ISE conditioning (provided by the organohydrogel coupling). By coupling the sensing interface with an ISE-specific touch-based sensing signal interpretation framework, lithium influx monitoring was demonstrated using an ex-situ setup as well as in a human subject study, illustrating its suitability for non-invasive lithium adherence monitoring.

To further improve the reliability of the system and the temporal granularity of the readout, future work is needed to address the confounding factors associated with touch-based sensing (e.g., variation of natural perspiration rate and temperature). To this end, axillary sensors can be integrated to normalize the readout (Jachowicz, R.; Weremczuk, J.; Tarapata, G. Transepidermal Water Loss Sensor Based on Fast Dew Point Hygrometer. Sensors and Actuators A: Physical 2005, 123-124, 7-11. https://doi.org/10.1016/j.sna.2005.04.001). Once established, large-scale clinical investigation will be performed to correlate the sensor readouts with the circulating analyte concentration levels, where advanced machine learning-based algorithms can be utilized. It is envisioned that the convergence of these efforts can ultimately enable decentralized lithium pharmacotherapy management that can promote patient outcomes.

Materials and Methods

Materials and Reagents

Agarose, bovine serum albumin (BSA), glutaraldehyde solution (25 wt. %), m-phenylenediamine, d-(+)-glucose, sodium L-lactate, potassium chloride (KCl), sodium chloride (NaCl), uric acid (UA), chitosan (high molecular weight), L-tyrosine, L-tryptophan, ascorbic acid (AA), Nafion perfluorinated resin solution (5 wt. %), alcohol oxidase (AOx) from *Pichia pastoris* (10-40 units/mg protein), chloroplatinic acid hexahydrate ($H_2PtCl_6 \cdot 6H_2O$), formic acid, sulfuric acid ($H_2SO_4$), and APAP were purchased from Sigma-Aldrich. Phosphate-buffered saline (PBS, 1×, pH 7.2; Gibco), ethanol, and all the reagents used in the high-performance liquid chromatography were purchased from Fisher Scientific. Polyethylene terephthalate (PET, 100 μm thick) was purchased from MG Chemicals. Double-sided tape (170 μm thick, 9474LE 300LSE) and Scotch single-sided self-seal laminating sheets were purchased from 3M Science. BDDE sensor (reference electrode: silver; counter electrode: carbon) was purchased from Metrohm USA. Silver-silver chloride (Ag/AgCl) ink was purchased from Ercon Incorporated. Polycarbonate membrane (thickness: 10 μm, pore size: 0.2 μm, pore density: $3 \times 108\ cm^{-2}$) was purchased from Sterlitech.

TH-Sensor Fabrication

The thin hydrogel was prepared using a vertically-assembled mold, which consists of a glass substrate, a double-sided tape layer, and a PET capping layer. PET and tape layers were patterned by laser cutting (VLS2.30, Universal Laser Systems) to form hydrogel chambers and access ports. Hydrogel was prepared by dissolving agarose powder (2 wt. %) in a PBS solution (80° C. water bath for 20 min). The solution was then injected into the assembled mold. Following the sufficient hydrogel gelation (~10 min), the tape/PET layers were removed, and the hydrogel was picked up. To further decrease its thickness, the hydrogel was dried for 3 hours in an ambient environment, and then rehydrated with PBS solution. The thickness of the thin hydrogel was measured to be 220±20 μm (see FIG. 8).

The ethanol sensor was fabricated by modifying the gold electrodes, which were patterned on a PET substrate with the aid of a shadow mask (200-nm-thick gold on a 30 nm-thick chromium as an adhesion layer, working electrode diameter:

1.2 mm). All the electrochemical deposition/measurement experiments were performed using CH1660E or CHI1040C electrochemical workstation (CH Instruments, Inc.). First, PtNPs were deposited on the gold electrode via an amperometric method (−0.2 V vs. Ag/AgCl, 720 s). The PtNP deposition solution contained 2.5 mM $H_2PtCl_6$ and 1.5 mM formic acid. Then a PPD layer was electrochemically deposited onto the PtNPs/Au electrode (0.85 V vs. Ag/AgCl, 120 s) using a PBS solution containing 5 mM m-phenylenediamine. To immobilize AOx, 1.2 μL AOx-BSA solution (34.67 mg/mL AOx and 16.67 mg/mLBSA) was dropped onto the PPD/PtNPs/Au electrode and dried for 30 min at room temperature. The electrode was further coated by 1.2 μL 0.5 wt. % chitosan solution, which was prepared by dissolving chitosan in a 0.25% acetic acid solution at 60° C. for 30 min. Finally, a 1.6 μL 0.6% glutaraldehyde solution was dropped on top of the sensor surface to crosslink the AOx, BSA and chitosan. All sensors were dried at 4° C. overnight before use. The reference electrode was fabricated by dropping ~2 μL Ag/AgCl ink onto the gold substrate, followed by drying at 65° C. for 30 min. The reference electrode was fabricated before the enzyme coating step to prevent the heat-induced AOx deactivation.

The APAP sensor was fabricated following our previously reported protocol (Id.). The BDDE was cleaned by repetitive cyclic voltammetry (CV) scanning in 0.5 M $H_2SO_4$ solution. The CV scanning was performed in the potential range of −0.5 V to 1.5 V (vs. Ag/AgCl; scan rate: 0.5 V/s) until a stable voltammogram was obtained. Nafion coating was performed by drop casting 1.8 μL 5 wt. % Nafion solution onto the working electrode, followed by a drying step in an ambient environment. To form TH-sensors, freshly prepared hydrogels were mounted onto the corresponding electrochemical sensors right before testing.

Microfluidic Artificial Fingertip Fabrication and Characterization

The construction of the microfluidic artificial fingertip builds upon a previously reported work by Heikenfeld et al. (Id.). Specifically, multiple layers were vertically aligned on a polystyrene substrate: 1) two layers of double-sided tape and a single PET layer to form the microfluidic chamber; 2) a single layer of double-sided tape with laser-patterned μ-pores; 3) a porous polycarbonate film; and 4) a scotch tape layer with laser-patterned μ-pores. All the geometric features were defined by AutoCAD (Autodesk) and realized by laser cutting. The sensor interfacing area of the artificial fingertip was adjusted according to the tested sensors' dimensions. Upon its construction, the artificial fingertip was connected to a programmable syringe pump (PHD ULTRATMCP, Harvard Apparatus), which delivered input fluid with different compositions and at adjustable flow rates (300-1000 nL/min/cm$^2$). To monitor the hydraulic pressure of the developed artificial fingertip, the assembled device was connected to a pressure sensor (Blood Pressure Transducers, APT 300, Harvard Apparatus) and a transducer amplifier module (TAM-D, Harvard Apparatus).

Ex-Situ TH-Sensor Characterization

The sensitivity and the selectivity of ethanol and APAP sensors were characterized using a standard electrochemical cell (reference electrode: Ag/AgCl, counter electrode: platinum) in the PBS solution. The ethanol sensor was tested by performing amperometric measurement at 0.5 V vs. Ag/AgCl. The APAP sensor was tested using differential pulse voltammetry (DPV, increment: 5 mV, amplitude: 50 mV, pulse width: 0.1 s, sampling width: 16.7 ms, and pulse period: 0.5 s). The ex-situ TH-sensor characterization was performed using the artificial fingertip with the same electrochemical testing methods. For the ethanol TH-sensor, the amperometric response of the TH-sensor was recorded continuously. After a stable amperometric baseline was obtained, the TH-sensor was mounted onto the artificial fingertip. The measured amperometric current was linearly fitted (for the duration of measurement of 0-60 s, after contacting the artificial fingertip). The derived current slope was considered as the sensor signal. For the APAP TH-sensor, a DPV scan was performed 3 min after mounting the sensor onto the artificial fingertip. The baseline estimation and voltammetric signal extraction were performed using MATLAB (MathWorks) following our previously reported analytical framework (Id.). For all the TH-sensor testing, a new hydrogel was used for each measurement. To characterize the effect of pressing force, weights were used to emulate force exertion with different strengths.

In-Situ TH-Sensor Characterization

Two human subjects participated in the characterization of each type of TH-sensor. For each trial, the subjects were instructed to wash their index fingertips with deionized (DI) water before testing and to rinse their mouth with cold water immediately after the beverage/medication intake (to avoid contamination from residue). Touch-based measurements were performed using corresponding TH-sensors before and at intermittent time points after the beverage/medication intake. The water loss from the fingertip was monitored by an evaporimeter (VapoMeter, Delfin Technologies). The fingertip temperature was monitored by a thermocouple (HT-9815, RISEPRO). For ethanol measurement, the amperometric current was linearly-fitted (for the duration of measurement of 10-30 s, after finger pressing) and the derived current slope was considered as the sensor signal. BAC was estimated using an alcohol breathalyzer (S80, BACtrack Inc.). The subject was provided with ~100 mL alcoholic beverages (12.5%, from the local market). For APAP measurement, a DPV scan was performed 3 min after finger pressing, and the acquired readout was analyzed using the same analytical framework as the ex-situ study. Saliva samples were collected by direct salivation with the aid of the Saliva Collection Aid (Salimetrics) and analyzed using the liquid chromatography with tandem mass spectrometry following our previous established protocol (Id.). The experiments were performed in accordance with the subjects' originally-scheduled medication intake (Regular Strength Pain Relief, CVS Health, containing 650 mg APAP in total).

FEA of the Analyte Flux

FEA software, COMSOL 5.2, was used to simulate the analyte concentration profile within a hydrogel layer for different levels of analyte flux inputs. In the simulation software, "transport of diluted species" simulation package was employed in the context of a 3D hydrogel structure with the same size used in the experiment. Input analyte was introduced from the top surface of the hydrogel with the same flux levels as the ethanol TH-sensor ex-situ testing experiment (concentration range: 0-10 mM, flow rate: 320 nL/min/cm$^2$). The analyte flux for the other surface boundaries was set to zero. The diffusion coefficient of target analyte (here, ethanol) in the hydrogel was set as $9\times10^{-6}$ cm$^2$ s$^{-1}$ (B. A. Westrin, A. Axelsson, A diaphragm diffusion cell applied to ethanol diffusion in agarose gel: A reproducibility study. Biotechnol. Tech. 5, 303-306 (1991)). The analyte concentration at the vicinity of the sensor surface (at its midpoint) was extracted to infer the sensor's response (assuming a mass transport limitation scenario).

PPG Signal Acquisition and Processing

The PPG sensing interface was constructed using an integrated PPG-based sensor module (MAX30101, Maxim Integrated Inc.) with a sampling rate of 80 Hz. The sensor module consists of a red and an IR light-emitting diode (red: 660 nm, IR: 880 nm), as well as a photodiode to detect the tissue-reflected light. A standard pulse oximeter (Zacurate Pro Series 500DL) was utilized to validate the sensor readout. The pulse oximeter was placed on a different fingertip of the subject's same hand. Continuous HR and $SpO_2$ readings from the standard pulse oximeter were video-recorded and compared with the readouts from the developed sensing interface. The PPG readout of the sensing interface was processed using MATLAB. Accordingly, upon signal smoothing, the peaks and troughs for both wavelengths were extracted using a local minima-maxima finding algorithm.

The HR was extracted by calculating the time interval between consecutive systolic peaks (average of 6 consecutive peaks). To derive the $SpO_2$ level, the non-pulsatile DC component and the pulsatile AC component for both wavelengths were extracted (DCred, DCIR, ACred, ACIR). For each peak-trough pair, the trough level was used as the DC component and the difference between the peak and trough levels was used as the AC component. Then, the ratio of the normalized red and IR readings (Rred/IR) for each peak-trough peak was determined as $$Rred/IR = ACred/DCredACIR/DCIR$$

The $SpO_2$ levels were estimated following a previously reported simplified linear calibration approach (T. Tamura, Current progress of photoplethysmography and $SpO_2$ for health monitoring. Biomed. Eng. Lett. 9, 21-36 (2019)), where the measurements by the standard pulse oximeter served as reference.

Fingerprint Acquisition and User Identification

The fingerprint sensing interface was constructed using a capacitive fingerprint scanner (AS-108M, Sparkfun). The acquired fingerprint image was processed using MATLAB following a previously reported algorithm (A. K. Jain, J. Feng, K. Nandakumar, Fingerprint matching. Computer. 43, 36-44 (2010); V. K. Alilou, Simple fingerprint matching (2020; https://github.com/alilou63/fingerprint). Briefly, for both query and template fingerprints, upon performing a feature enhancement step, the friction ridges were identified, and the minutiae pattern was extracted and outputted as a list of minutiae features. To assess the degree of similarity, different permutations of one-to-one pairing between the query and template minutiae features were constructed. To account for the slight differences in fingerprint input angle, the rotated versions of the minutiae patterns were also constructed (relatively rotated within 5°) and compared. For each pairing permutation, the paired minutiae features were compared individually: two minutiae were defined as a match if their relative distance and ridge direction difference were both below defined thresholds (threshold distance: 15 pixels, threshold direction difference: 14°). The degree of similarity (s) was determined by considering the permutation that produced the maximum number of matched pairs (following the definition presented in the Results section). The query fingerprint was determined to match the template if the calculated s was greater than the defined threshold of 50%.

CBS Construction

The fingerprint-based CBS follows a previously reported fuzzy vault scheme (implemented in MATLAB) (J. Woogerd, Fuzzy vault (2021; https://github.com/jwoogerd/fuzzy_vault). For data encryption, a sequence of integers was formed (secret) by appending the TH-sensor, HR, and $SpO_2$ readouts (each 3 digits long), together with a single-digit indicative of the feedback status (0: medication supply request rejected; 1: medication supply request granted; 2: medication intake pending; and 3: medication intake verified). A 3-bit cyclic redundancy check (CRC-3) was calculated based on the secret (with the aid of the standard CRC-3 generating polynomial), and the equivalent decimal value was derived and prepended to the secret. Similarly, an error-prevention digit ("0") was appended to the secret to mitigate the influence of fitting error in the subsequent decryption process. The modified secret was then divided into four segments, each serving as a coefficient in a third-degree polynomial f(x) expression. The 10-digit biometric key {xi}(i=1 to 10) was generated using the minutiae pattern of the template fingerprint by calculating the relative distance of the extracted minutiae features with respect to a given extracted feature as a reference. Then the generated key was projected onto the polynomial to create a set of genuine points {(xi, f(xi))}. With the aid of a random number generator, a set of chaff points was created as {(aj, bj)}(j=1 to 40), where aj≠ai (i=1 to 10) and bj≠f(aj). The vault {(uk, vk)}(k=1 to 50) was created by assembling and scrambling the genuine and chaff sets.

To decrypt the secret, a biometric key {yi}(i=1 to 10) was first generated using the query fingerprint similar to the encryption procedure. Then {yi} was compared with the abscissa values of the vault {uk}: if any yi was equal to uk, the corresponding (uk, vk) was identified as a genuine point candidate. The genuine point candidates were used to reconstruct the third-degree polynomial of best fit (with the aid of a polynomial fitting function). The original secret was then retrieved based on the coefficients of the reconstructed polynomial. For the entries where the number of genuine point candidates were insufficient for polynomial fitting or that the CRC decoding failed, the decryption process was considered and labelled as a "Fail". Otherwise, the retrieved secret was presented as the corresponding bio-input values to the user.

CB-HMI Construction

The data acquisition module of an example embodiment includes two printed circuit boards (PCBs): a primary PCB to host the TH-sensor, the fingerprint scanner, and the PPG sensor, and a secondary PCB, which hosts the signal conditioning circuitry and a Bluetooth module (HM-11; Seeed Technology Co.). The TH-sensor was connected to the primary PCB with the aid of a flexible cable (Molex) and a double-sided adhesive anisotropic conductive film (9703; 3M). The secondary PCB was interfaced with a data processing module (implemented on Raspberry Pi 3 model B+, Raspberry Pi Foundation). To acquire the biochemical indices, the excitation potential waveform was applied to the corresponding TH-sensor with the aid of a 16-bit digital-to-analog converter (DAC, DAC8552, Texas Instruments). For ethanol sensing the excitation waveform was a constant voltage, and for APAP sensing the waveform followed a DPV format (following the same parameters as respective potentiostat measurements). The current response of the TH-sensors was converted into a digital voltage output with the aid of a transfer impedance amplifier (TIA) (LT1462; Linea Technology) and a 24-bit analog-to-digital converter (ADC) (ADS1256; Texas Instruments). The PPG sensor and the fingerprint scanner directly communicated with the Raspberry Pi through the inter-integrated circuit (I2C) protocol and the universal asynchronous receiver-transmitter (UART) interface, respectively. The MATLAB data processing codes (implementing the inference, bio-authentication, and encryption algorithms) were loaded on the Raspberry Pi.

A single, miniaturized, rechargeable lithium-ion polymer battery with a nominal voltage of 3.7 V was used to power the PCBs and the Raspberry Pi.

Construction of CB-HMI-Enabled Systems

For both in-vehicle and medication dispensing systems, the Raspberry Pi was connected to a 1.44-in color thin-film-transistor LCD screen (SF-TS144C-9082A-N; Shenzhen SAEF Technology) to provide visual feedback. The in-vehicle safety system was constructed by mounting the CB-HMI and the LCD screen onto a steering wheel (via a double-sided tape). The medication dispensing system was constructed by repurposing a motorized box (Useless Box, Calary). The front panel of the box was laser-patterned (Speedy 300, Trotec) to accommodate the CB-HMI and the LCD screen. The robotic arm movement was controlled by the Raspberry Pi with the aid of a motor driver (L298N; STMicroelectronics). The acquired and in-situ encrypted bio-inputs were communicated (via Bluetooth) to a user interface (e.g., a laptop), which in turn served as an intermediary terminal for data transmission to a cloud server (here, a custom-developed Google Cloud platform).

Human Subject Testing Using the CB-HMI-Enabled Systems

For the in-vehicle system, the fingerprint of the vehicle owner was collected and stored in the Raspberry Pi as a template. For each entry, the subject was instructed (via LCD) to press the fingertip onto the CB-HMI until all the bio-inputs were acquired (~40 s). During this period, the ethanol (10-30 s post fingertip pressing), PPG, and fingerprint readouts were acquired sequentially. The raw readouts were transmitted to the Raspberry Pi for data processing. Bio-authentication was performed by comparing the processed data with the corresponding thresholds. The determined alcohol state of the subject, the derived HR and $SpO_2$ information, and the concluded bio-authentication status were transmitted and displayed on the LCD screen. For the medication dispensing system, the fingerprint information was also collected and stored in the Raspberry Pi as a template. For each entry, the subject was instructed (via LCD) to press the fingertip onto the CB-HMI for ~30 s. During the fingertip pressing period, the fingerprint and the PPG readouts were acquired sequentially. The DPV scanning was performed afterwards (~30 s). All the raw readouts were transmitted to the Raspberry Pi for data processing, bio-authentication, and medication dispensing (if applicable). The interpreted bio-inputs and the feedback status were transmitted to and displayed on the LCD screen. The conducted human subject experiments were performed in compliance with the protocols that have been approved by the Institutional Review Board at the University of California, Los Angeles (IRB No. 17-000170). All subjects gave written informed consent before participation in the study.

Example TOH Materials and Methods

Materials and Reagents: All the chemicals were purchased from Sigma-Aldrich (MO, USA), unless otherwise stated. Polyethylene terephthalate (PET, 100 m thick) was purchased from MG Chemicals (CA, USA). Silver-silver chloride (Ag/AgCl) ink was purchased from Ercon Incorporated (MA, USA). Aqueous dispersion of PEDT:PSS conductive polymer (Clevios PH 1000) was purchased from Heraeus Heraeus Precious Metals North America Daychem LLC (OH, USA). The artificial sweat solution was purchased from Pickering Laboratories, Inc. (CA, USA) using a customized composition.

Fabrication and characterization of TOH. To fabricate TOH, 2 wt. % agarose and 3 wt. % artificial sweat solution (unless otherwise stated) were first mixed with a bi-solvent solution consisting of 80% deionized (DI) water and 20% glycerol. The mixture was incubated in the 80° C. water bath for 30 min. The resultant clear solution was then injected into vertically-assembled molds (fabricated following our previous protocol (Id.)). After sufficient cooling, a rectangular organohydrogel was formed. The gel was removed from the mold and dried overnight to allow for the evaporation of free water. The fabricated TOH was stored in an ambient environment if not used. To fabricate the lithium-spiked TOH, 1 mM lithium chloride (LiCl) was added into the gel solution before gelation. The thickness of TOH was measured to be 59±10 μm (n=6). The measurement was performed under a microscope using a glass slide with a defined thickness as the reference.

Fabrication and characterization of lithium ISE. The lithium ISE was fabricated on a gold electrode, which was patterned on a PET substrate with the aid of a shadow mask (30 nm chromium/200 nm gold, electrode diameter: 2.4 mm). First, 2.5 μL PEDOT:PSS solution was dropped onto the gold electrode and then dried at room temperature (~30 min). The acquired electrode was baked at 60° C. for 30 min to facilitate PEDOT conjugation. For ISM coating, the PEDOT:PSS electrode was dipped into a lithium ISM cocktail for 10 dip cycles (2 s each) and the sensor was dried for 5 min between dips. To prepare the cocktail (cocktail 1), 3 mg Li Ionophore VI, 2 mg potassium tetrakis (4-chlorophenyl)borate (KTCPB), 84 mg polyvinyl chloride (PVC), and 203 μL 2-nitrophenyl octyl ether (NPOE) were dissolved into 3 mL tetrahydrofuran (THE). To compare the performance of different ISM in our context at hand, a second widely-used lithium ISM cocktail (cocktail 2) was also prepared. This cocktail contained 4.5 mg Li Ionophore VI, 1.5 mg KTCPB, 4.5 mg trioctylphosphine oxide (TOPO), 84 mg PVC, and 198 μL NPOE in 3 mL THF. The fabricated ISEs were conditioned in a 10 mM LiCl artificial sweat solution for 2 hours before use. Standalone ISE characterizations were performed using a standard electrochemical cell (versus aqueous Ag/AgCl reference electrode, CH Instruments, Inc. [TX, USA]). All the electrochemical measurements were performed using CHI660E or CHI1040C electrochemical workstation (CH Instruments, Inc.).

To fabricate the reference electrode, Ag/AgCl ink was first dropped onto the same gold electrode for ISE construction and dried at 65° C. for 30 min. Then a polyvinyl butyral/sodium chloride (PVB/NaCl) solution was dropped onto the Ag/AgCl electrode 3 times (4 μL per time; 10 min interval between dropping) to eliminate the interference of Cl- concentration variation. The solution was prepared by dissolving 79 mg PVB and 50 mg NaCl into 1 mL methanol. The fabricated/conditioned lithium ISE and reference electrode were paired and taped on a PET substrate to form a full sensor.

Ex-situ TOH-ISE characterizations. The TOH was mounted onto a lithium sensor to form a TOH-ISE unit. The TOH-ISE was stored in an ambient environment if not used. The storage of the coupled unit also serves for in-situ ISE conditioning. The unit was conditioned for at least overnight before any testing if otherwise stated.

The TOH-ISE's response to a lithium flux input was characterized by coupling with a microfluidic artificial fingertip setup that was fabricated following a previous work (Id.). In the experiment, the potentiometric readout of the TOH-ISE was recorded continuously. After a stable baseline was obtained, the TOH-ISE was mounted onto the artificial fingertip, which delivered input fluid with different lithium concentration levels at a constant flow rate (320 nL/min/cm$^2$). Potentiometric readout between 15-100 s post artificial fingertip contact was fitted into the described signal interpretation model (equation (2) in the main text) to extract the flux-related signal s (Matlab). In the fitting process, we used the experimentally determined value of the slope m (57 mV/dec, from the standalone ISE characterization) to avoid overfitting. The starting time point (15 s) was experimentally determined to account for the analyte diffusion time and the contact-induced disturbance. A new TOH was used for each measurement. To characterize the effect of pressing force, weights were used to emulate force exertion with different strengths.

In-situ TOH-ISE characterization. One subject under lithium-based pharmacotherapy (900 mg lithium carbonate per day) and three healthy subjects (without lithium-based medication history) were recruited in the study. For each touch-based entry, the subjects were instructed to wash their index or middle fingertips with DI water before testing. The acquired potentiometric readouts were processed using the same method as the ex-situ experiments to extract the sensing signal. For saliva collection, the subjects were instructed to rinse their mouth with cold water before collection. The samples were collected via direct salivation using a Saliva Collection Aid (Salimetrics, CA, USA). The salivary lithium was quantified using a colorimetric lithium assay kit (Abcam ab235613, MA, USA) and Nanodrop One (Thermo Fisher, MA, USA).

Institutional Review Board Approval for Human Subject Testing. The conducted human subject experiments were performed in compliance with the protocols that have been approved by the Institutional Review Board at the University of California, Los Angeles (IRB No. 17-000170). All subjects gave written informed consent before participation in the study.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

Although the present embodiments have been particularly described with reference to preferred examples thereof, it should be readily apparent to those of ordinary skill in the art that changes and modifications in the form and details may be made without departing from the spirit and scope of the present disclosure. It is intended that the appended claims encompass such changes and modifications.

What is claimed is:

1. A device comprising:

a multimodal cryptographic bio-human machine interface ("CB-HMI") configured to translate a user's touch-based entries and/or other biomarkers into encrypted biometric indices, the CB-HMI including a service activator that receives the encrypted biometric indices and determines whether to activate a service for the user based on an analysis of biomarkers and identity information included in the encrypted biometric indices.

2. The device of claim 1, wherein the CB-HMI further includes thin hydrogel-coated chemical sensors and inference algorithms to non-invasively acquire biomarkers and/or biochemical indices such as circulating molecules that partition onto the skin.

3. The device of claim 2, wherein the circulating molecules comprise one or both of ethanol and acetaminophen.

4. The device of claim 1, wherein the CB-HMI further includes physical sensors and associated algorithms to simultaneously acquire one or more of the user's heart rate, blood oxygen level, blood pressure, respiratory rate, and fingerprint minutiae pattern.

5. The device of claim 1, wherein the CB-HMI is further configured to acquire physiologically-relevant readouts of target bio-indices and to biometrically encrypt and decrypt these bio-indices in-situ using a fingerprint sensor.

6. The device of claim 1, wherein the service is associated with driving safety and medication use.

7. The device of claim 6 wherein the service activator is included in a vehicle activation system.

8. The device of claim 6 wherein the service activator is included in a medication dispensing system.

9. The device of claim 1, wherein the CB-HMI includes a gel-coated lithium sensing interface to collect and analyze partitioned lithium ions on fingertips in-situ.

10. The device of claim 1, wherein the biomarkers included in the analysis include one or more of the user's heart rate, blood oxygen level, blood pressure and respiratory rate.

11. The device of claim 1, wherein the biomarkers included in the analysis include a detected level of ethanol in the user's fingertip.

12. The device of claim 11, wherein the detected level of ethanol is determined from an analysis of the user's sweat.

13. The device of claim 1, wherein the biomarkers included in the analysis include a detected level of acetaminophen in the user's fingertip.

14. The device of claim 13, wherein the detected level of acetaminophen is determined from an analysis of the user's sweat.

15. A device comprising:

a touch-based non-invasive lithium monitoring solution, including a gel-coated lithium sensing interface to collect and analyze partitioned lithium ions on fingertips in-situ.

16. The device of claim 15, wherein the interface comprises a thin organohydrogel-coated lithium ion-selective electrode (TOH-ISE), wherein the TOH simultaneously addresses stability challenges associated with the sensing interface.

17. The device of claim 16, wherein the TOH comprises a water-glycerol bi-solvent matrix, having an anti-dehydration property.

18. The device of claim 16, wherein when coupled with a lithium ISE, the TOH coating serves as a controlled micro-environment to condition the ISE in-situ.

19. The device of claim 16, wherein the TOH-ISE includes a ISE-specific signal interpretation framework that is capable of extracting the lithium flux information from touch-based readouts.

* * * * *